(12) United States Patent
Schilling et al.

(10) Patent No.: US 11,242,369 B1
(45) Date of Patent: Feb. 8, 2022

(54) N-TERMINAL CAPPING MODULES OF ANKYRIN REPEAT DOMAINS

(71) Applicant: Athebio AG, Zurich-Schlieren (CH)

(72) Inventors: Johannes Schilling, Zurich-Schlieren (CH); Patrik Forrer, Zurich-Schlieren (CH)

(73) Assignee: Athebio AG, Zurich-Schlieren (CH)

( * ) Notice: Subject to any disclaimer, the term of this patent is extended or adjusted under 35 U.S.C. 154(b) by 0 days.

(21) Appl. No.: 17/232,470

(22) Filed: Apr. 16, 2021

(30) Foreign Application Priority Data

Aug. 18, 2020 (EP) .................... 20191632

(51) Int. Cl.
  *C07K 14/47* (2006.01)
  *A61K 38/00* (2006.01)

(52) U.S. Cl.
  CPC .............. *C07K 14/47* (2013.01); *A61K 38/00* (2013.01)

(58) Field of Classification Search
  None
  See application file for complete search history.

(56) References Cited

U.S. PATENT DOCUMENTS 9,221,892 B2 * 12/2015 Binz .................... C07K 14/001

FOREIGN PATENT DOCUMENTS

| WO | 2012069655 A2 | 5/2012 |
|---|---|---|
| WO | 2014191574 A1 | 12/2014 |
| WO | 2016023898 A2 | 2/2016 |
| WO | 2020190852 A2 | 9/2020 |
| WO | 2021116462 A1 | 6/2021 |
| WO | 2021116469 A2 | 6/2021 |
| WO | 2021116470 A2 | 6/2021 |
| WO | 2021229067 A1 | 11/2021 |
| WO | 2021229076 A1 | 11/2021 |

OTHER PUBLICATIONS

Mosavi et al, "The Ankyrin Repeat as Molecular Architecture for Protein Recognition" Protein Science 13: 1435-1448. (Year: 2004).*
Interlandi et al., "Characterization and further stabilization of designed ankyrin repeat proteins by combining molecular dynamics simulations and experiments." Journal of Molecular Biology 375(3): 837-854 (2008).
Kramer et al. "Structural determinants for improved stability of designed ankyrin repeat proteins with a redesigned C-capping module." Journal of Molecular Biology 404(3): 381-391 (2010).
Plückthun. "Designed ankyrin repeat proteins (DARPins): binding proteins for research, diagnostics, and therapy." Annual Review of Pharmacology and Toxicology 55(1): 489-511 (2015).
Wetzel et al. "Residue-resolved stability of full-consensus ankyrin repeat proteins probed by NMR." Journal of Molecular Biology 402(1): 241-258 (2010).
Communication pursuant to Article 94(3) EPC issued in corresponding EP Application No. 20191632.7; dated Apr. 30, 2021; 5 pp.

* cited by examiner

*Primary Examiner* — Anand U Desai
(74) *Attorney, Agent, or Firm* — Ronald I. Eisenstein; David S. Resnick; Nicole D. Kling

(57) ABSTRACT

Described herein are proteins comprising an ankyrin repeat domain having an N-terminal capping module with improved properties, as well as corresponding protein libraries, pharmaceutical compositions and nucleic acids encoding such proteins. In other aspects, the disclosure relates to methods using such proteins, corresponding protein libraries or pharmaceutical compositions.

12 Claims, 3 Drawing Sheets

Specification includes a Sequence Listing.

N-TERMINAL CAPPING MODULES OF ANKYRIN REPEAT DOMAINS

CROSS-REFERENCE TO RELATED APPLICATIONS

This application claims benefit under 35 U.S.C. § 119(a) of EP Application No. EP20191632.7 filed Aug. 18, 2020, the contents of which are incorporated herein by reference in their entirety.

SEQUENCE LISTING

The sequence listing of the present application has been submitted electronically via EFS-Web as an ASCII formatted sequence listing with a file name "2021-04-16-Sequence-Listing-Athebio-AG-190010USPT.txt", creation date of Apr. 16, 2021, and a size of 70,986 bytes. The sequence listing submitted via EFS-Web is part of the specification and is herein incorporated by reference in its entirety.

FIELD OF THE INVENTION

The present invention relates to proteins comprising an ankyrin repeat domain with an N-terminal capping module conferring improved properties to the ankyrin repeat domain, as well as related products and the use of such proteins in methods of treatment.

BACKGROUND OF THE INVENTION

Different classes of specific binding proteins have evolved in nature, the most widely known class being immunoglobulins of vertebrates. Another class of specific binding proteins are repeat proteins. Similar to the role that immunoglobulins play in vertebrates, repeat proteins were found to be involved in the adaptive immune system of jawless fish. However, repeat proteins play a much wider role beyond this function and mediate protein-protein interactions across all phyla to fulfill diverse biological functions. In fact, they constitute the largest group of natural proteins mediating specific binding (e.g. reviewed in Forrer, P., et al., FEBS letters 539, 2-6, 2003). Repeat proteins bind their targets via the repeat domain, which is made up of a variable number of repeats that stack on each other through their conserved interfaces to create the compactly folded repeat domain. Specific target binding is then achieved through variable residues on the surface of the repeat domain (Forrer 2003, loc. cit. and WO 2002/020565).

Ankyrin repeat proteins are a well-studied class of repeat proteins. The ankyrin repeat usually comprises 33 amino acid residues forming two antiparallel alpha-helices and a beta-turn. The folded ankyrin repeat domain comprising the stacked ankyrin repeats has a right-handed solenoid structure with a compact hydrophobic core and a large binding surface, which allows it to adapt to its respective binding partners (e.g. Binz, H. K., et al., Nat. Biotechnol. 22, 575-582, 2004).

Plückthun and coworkers derived a consensus sequence motif from naturally occurring ankyrin repeats (e.g., Binz, H. K., et al., J. Mol. Biol., 332, 489-503, 2003 and WO 2002/020565). The derived ankyrin repeat consensus motif is 33-amino acid residues long and comprises fixed and variable positions. The fixed positions correspond mainly to framework residues that are primarily responsible for the structural integrity of the ankyrin repeats, in particular, for the interrepeat stacking interactions. The variable positions correspond to surface-exposed residues that do not strongly contribute to the structural integrity of the ankyrin repeats; but, are potentially involved in target binding (though surface-exposed framework residues may be involved in target binding too).

Libraries of proteins were then created having an ankyrin repeat domain with internal ankyrin repeats that were based on such ankyrin repeat consensus motif (Binz, 2004, loc. cit.). Certain variable positions of the consensus motif were randomized in each internal ankyrin repeat to allow for the binding to different targets, thereby creating the diversity of the library. In order to avoid aggregation of ankyrin repeat domains consisting only of internal ankyrin repeats, the internal ankyrin repeats were flanked by an N-terminal capping module and a C-terminal capping module to shield the hydrophobic core of the domain from the solvent (Forrer, 2003, loc. cit. and Binz, 2003, loc. cit.). These capping modules were based on the capping repeats of the human guanine-adenine-binding protein (GA-binding protein). Libraries composed of proteins with ankyrin repeat domains having one, two or three internal ankyrin repeats are referred to as an N1C, N2C and N3C library, respectively, wherein the "N" refers to the N-terminal capping module, "C" refers to the C-terminal capping module and the number to the number of internal ankyrin repeats (Binz, 2003, loc. cit).

Using such a synthetic library of designed ankyrin repeat proteins (DARPins), DARPins against specific targets can be selected with common selection methods, including phage display, ribosome display and yeast display, and were shown to have very favorable properties. While displaying binding specificities and affinities that are comparable to immunoglobulins, DARPins are much more robust and can be easily engineered into multispecific binding proteins that are easily expressed and purified. DARPins are well studied (e.g. Plückthun, A., Annu. Rev. Pharmacol. Toxicol. 55, 489-511, 2015).

Following the design of the original DARPin library by Plückthun and coworkers (Binz, 2003, loc. cit. and WO 2002/020565), it was shown that a mutation in the N-terminal capping module can increase the thermostability of an ankyrin repeat domain (WO 2012/069655).

There remains a need to further improve the properties of proteins comprising an ankyrin repeat domain, such as the thermostability of the ankyrin repeat domain.

SUMMARY OF THE INVENTION

The present invention is based on the discovery that specific mutations in the N-terminal capping module can significantly improve the properties of an ankyrin repeat domain. In particular, it has been found that the amino acid residue present at the position in the N-terminal capping module, which corresponds to position 15 of SEQ ID NO: 3, is of key importance for the thermostability of an ankyrin repeat domain. It has also been found that only a few amino acid residues in this position have a striking effect on thermostability. Furthermore, the effects of these mutations were transferable to ankyrin repeat domains with diverging sequences, demonstrating the general importance of this position in the N-terminal capping module for the thermostability of ankyrin repeat domains.

Accordingly, the present invention provides a protein comprising an ankyrin repeat domain, wherein the ankyrin repeat domain comprises an N-terminal capping module with a mutation in the position, which corresponds to position 15 of SEQ ID NO: 3.

In a further aspect, the present invention provides a protein library comprising such proteins.

In a further aspect, the present invention provides a method of selection using such protein libraries.

The present invention also provides pharmaceutical compositions comprising the proteins of the invention, nucleic acids encoding them or vectors or cells comprising said nucleic acids.

In a further aspect, the present invention provides a method of preparing a protein of the invention comprising culturing a cell having a nucleic acid encoding the protein of the invention under conditions allowing expression thereof and then purifying the expressed protein.

In a further aspect, the present invention relates to the proteins of the invention for use in a method of treatment.

Related compositions and methods are also provided, as will be apparent from the following detailed description.

FF, fraction folded in %; T, temperature in ° C.; P #95 and P #101 consist of the amino acid sequences of SEQ ID NO: 95 and SEQ ID NO: 101, respectively. P #101, but not P #95, comprises an improved N-terminal capping module of the invention.

Figure 2:
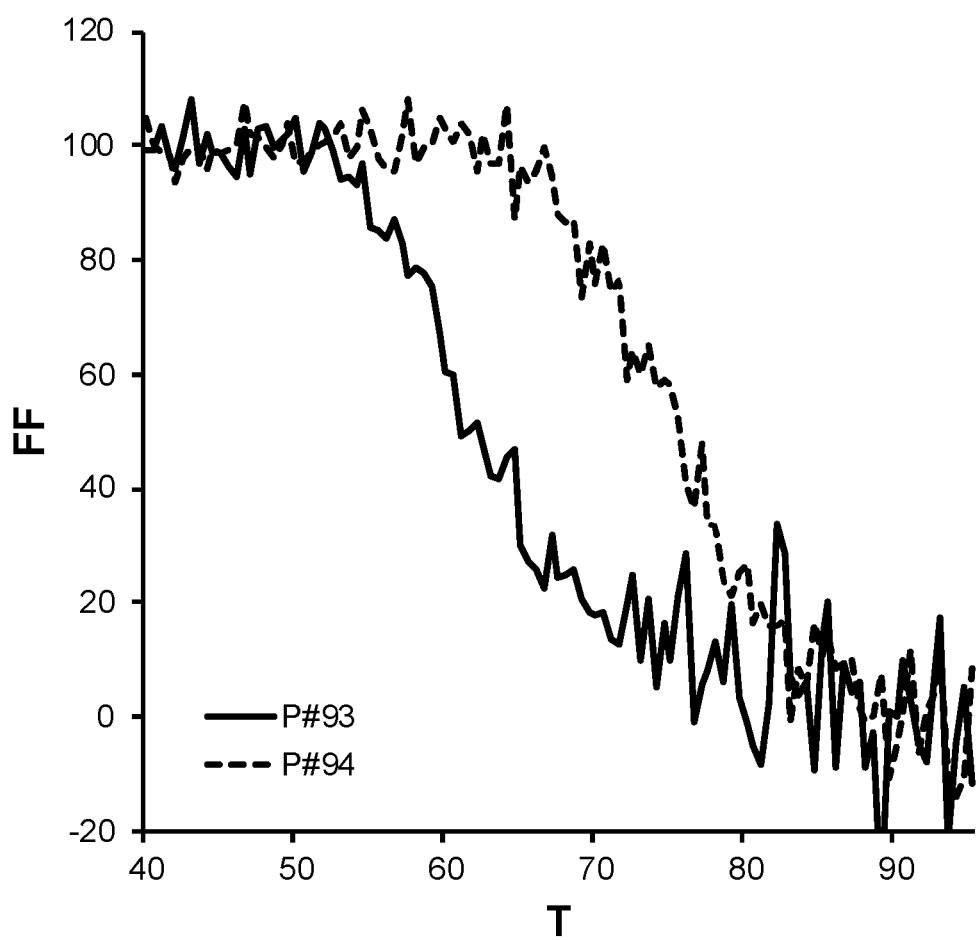

FIG. 2: Thermal stability of the designed ankyrin repeat proteins P #93 and P #94. Traces from thermal denaturation of P #93 and P #94 are shown. The thermal denaturation is followed by the CD signal at 222 nm in PBS at pH 7.4. The Tm values for P #93 and P #94 were estimated to be 62.1° C. and 75.2° C., respectively.

FF, fraction folded in %; T, temperature in ° C.; P #93 and P #94 consist of the amino acid sequences of SEQ ID NO:93 and SEQ ID NO:94, respectively. P #94, but not P #93, comprises an improved N-terminal capping module of the invention.

Figure 3:
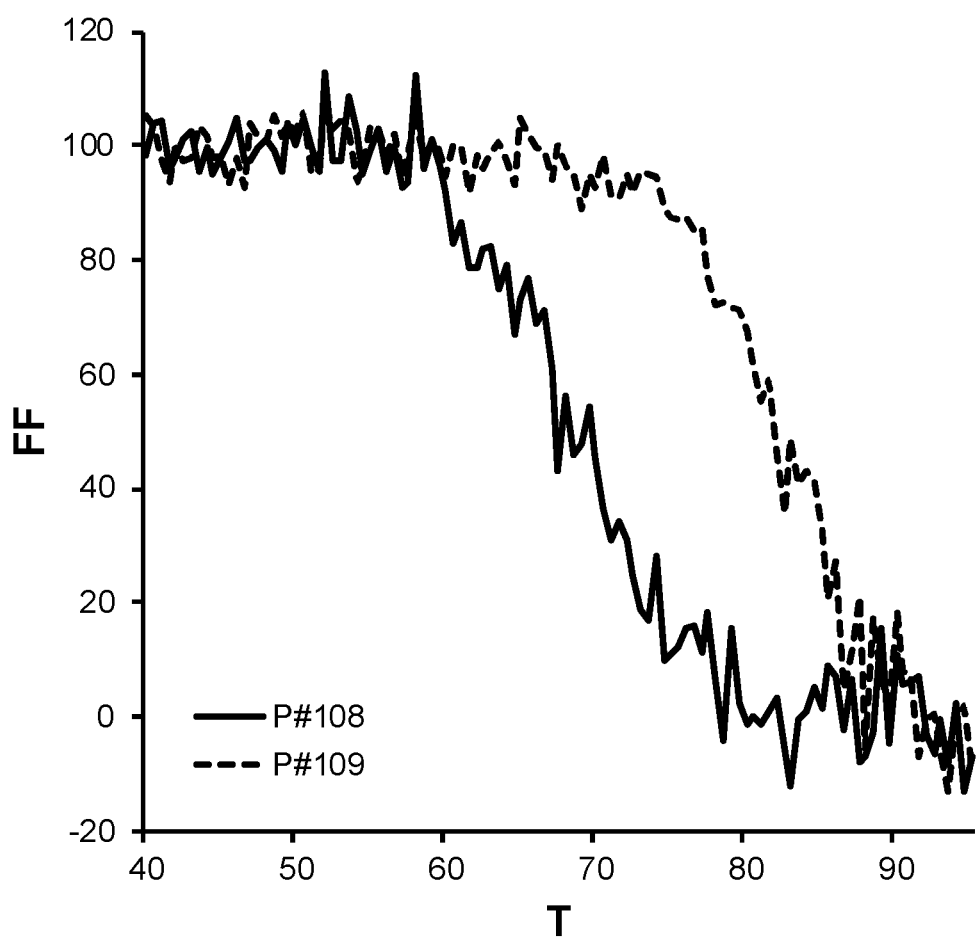

FIG. 3: Thermal stability of the designed ankyrin repeat proteins P #108 and P #109. Traces from thermal denaturation of proteins P #108 and P #109 are shown. The thermal denaturation is followed by the CD signal at 222 nm in PBS at pH 7.4. The Tm values for P #108 and P #109 were estimated to be 68.6° C. and 82.8° C., respectively.

FF, fraction folded in %; T, temperature in ° C.; P #108 and P #109 consist of the amino acid sequences of SEQ ID NO: 108 and SEQ ID NO: 109, respectively. P #109, but not P #108, comprises an improved N-terminal capping module of the invention.

DETAILED DESCRIPTION OF THE INVENTION

"A", "an", and "the" include plural reference unless the context clearly dictates otherwise. Thus, for example, reference to a protein comprising an ankyrin repeat domain refers to one or more such proteins.

An "ankyrin repeat" refers to a short sequence of amino acid residues forming a structural motif (e.g., SMART accession number: SM00248). Ankyrin repeats occur in consecutive copies, are involved in protein-protein interactions and the core of the ankyrin repeat forms a helix-loop-helix structure.

The term "ankyrin repeat domain" refers to a protein domain comprising an N-terminal capping module, a C-terminal capping module and one or more ankyrin repeats in between (also referred to as "internal ankyrin repeats"). An ankyrin repeat domain has a hydrophobic core, which is shielded on its N- and C-terminal end by N- and C-terminal capping modules, respectively, from the solvent. The folded ankyrin repeat domain has a right-handed solenoid structure with a large binding surface that is adaptable to specifically bind targets. The ankyrin repeat domain is generally very robust and can sustain a significant number of mutations, including substitutions, additions and deletions, without destroying its overall structure. The residues that contribute to the structural integrity of the ankyrin repeat domain, including the interrepeat interactions, are referred to as "framework residues", whereas the residues that contribute to target binding, either through direct interaction with the target or by influencing residues that directly interact with the target, e.g., by stabilizing them, are referred to as "target interaction residues". A single amino acid residue can be both—a framework and a target interaction residue—at the same time and framework residues and target interaction residues may be found not only in the internal ankyrin repeats, but also the N-terminal capping module and/or the C-terminal capping module.

The internal ankyrin repeats contribute to the structural stability of the ankyrin repeat domain due to their stacking interaction with the neighboring repeats. An internal ankyrin repeat usually consists of 33 amino acid residues.

The capping modules have a hydrophobic inside surface that is suitable for interacting with the adjacent internal ankyrin repeat and a hydrophilic outside surface to shield the hydrophobic core from the solvent. In some embodiments, the N-terminal capping module and/or the C-terminal capping module are a N-terminal capping repeat and/or C-terminal capping repeat, respectively, which have a similar or the same fold as the adjacent internal ankyrin repeat(s) and/or sequence similarities to said adjacent internal ankyrin repeat(s).

The terms "binding", "specific binding" or the like when used in reference to a target mean a binding interaction that is measurably different from a non-specific interaction, e.g., the interaction with a control molecule that is unrelated to the specific target. Control molecules that are commonly used to measure such non-specific interaction include bovine serum albumin, bovine casein and *Escherichia coli* maltose binding protein (unless, of course, the respective proteins were the target for the specific binding). In certain instances, the terms "binding", "specific binding" or the like mean that only the target is bound and substantially no other molecule. Specific binding can be determined, for instance, by measuring the dissociation constant (Kd) for the target and/or by comparing the binding to the target with the binding to a control molecule. The Kd can be measured by various conventional techniques, such as isothermal titration calorimetry, radioligand binding assay, fluorescence energy resonance transfer, and surface plasmon resonance. The binding specificity is generally measured in standardized solutions, such as PBS. For instance, the Kd for the target in PBS is at least 10, at least $10^2$, at least $10^3$ or at least $10^4$ times lower than the corresponding Kd for a control molecule that is unrelated to the specific target.

The term "designed ankyrin repeat protein" or "DARPin" refers to a non-natural protein comprising an ankyrin repeat domain. In some embodiments, such a DARPin has a repeat sequence motif that was derived from natural ankyrin repeats, e.g. by consensus design (see, e.g., Forrer et al., 2004 Chem Bio Chem, 5, 2, 183-189 and Binz 2003, loc. cit).

The term "fraction of refolded ankyrin repeat domains after thermal denaturation" refers to the fraction of ankyrin repeat domains that refold into their native state after thermal denaturation.

The term "library" as used in reference to a protein or nucleic acid library refers to a collection of proteins and nucleic acids, respectively.

The term "melting temperature" or "Tm" refers to the temperature at which 50% of the protein is unfolded in a certain buffer, e.g. PBS.

The term "modification", as used in reference to a specific amino acid sequence (e.g. the amino acid sequence of an internal ankyrin repeat or capping module), refers to one or more modification(s) of said amino acid sequence selected from the group consisting of deletions, insertions and/or substitutions. In some embodiments, the number of deletions and insertions is limited, for instance, to a combined number of deletions and insertions of not more than three, not more than two or not more than one of the total number of modification(s). Accordingly, if there is a total number of not more than 9 modifications, the number of deletions and insertions of those not more than 9 modifications may be limited to a combined number of insertions and deletions of not more than two. In some embodiments, the modification(s) are substitution(s) only. A substitution can be a substitution of an amino acid residue with, e.g., any of the naturally occurring amino acid residues. In some embodiments, the substitution of an amino acid residue is with an amino acid residue selected from the group consisting of A, D, E, F, H, I, K, L, M, N, Q, R, S, V, W and Y. In some embodiments, the substitution of an amino acid residue is with an amino acid residue selected from the group consisting of A, D, E, H, I, K, L, Q, R, S, V and Y. The following amino acid residues may, for instance, be particularly suitable for the respective position of the N-terminal capping module:

TABLE 1

| Position | Amino acid residue |
|---|---|
| 1 | A, E, N, Q, G, S, T, K, D, R, H, C |
| 2 | E, L, Q, M, K, R, C |
| 3 | G, D, S, A, C |
| 4 | A, R, T, S, N, Q, K, D, E, H, C |
| 5 | A, R, T, S, N, Q, K, D, E, H, C |
| 6 | A, L, N, S, D, C |
| 7 | L, I, V, A, N, T, S, D, C |
| 8 | E, D, Q, A, N, S, T, K, R, H, C |
| 9 | A |
| 10 | V, S, A, C |
| 11 | L, S, Q, K, R, A, H, D, E, C, T, N, F, W, Y |
| 12 | K, R, A, T, S, N, Q, D, E, H, C |
| 13 | G, C |
| 14 | N, S, T, A, D, E, K, Q, R, H, C |
| 15 | M, I, T, A, L, V, S, N, D, Q, K, R, E, C |
| 16 | D, A, N, Q, S, T, K, E, R, H, C |
| 17 | D, A, N, Q, S, T, K, E, R, H, C |
| 18 | T, A, S, I, L, V, C |
| 19 | R, E, D, K, A, N, Q, S, T, H, C |
| 20 | N, K, R, T, S, E, Q, A, D, H, C, I, V |
| 21 | N, S, L, A, C |
| 22 | I, A, V, M, T, L, S, N, C |
| 23 | R, S, Q, K, N, A, E, D, H, C |
| 24 | A, H, K, R, L, I, V, C, G |
| 25 | G |
| 26 | A |
| 27 | N, D, C |

TABLE 1-continued

| Position | Amino acid residue |
|---|---|
| 28 | T, V, S, P, A, C |
| 29 | D, N, C |
| 30 | A, C |

An amino acid substitution may be a conservative or non-conservative substitution. In some embodiments, substitutions only relate to conservative amino acid substitutions. A conservative amino acid substitution typically involves exchanging an amino acid residue by a different one having similar biophysical properties. For instance, the amino acid residues with a positively charged sidechain K, R and H, the amido acids with negatively charged sidechain E and D, the amino acid residue with a polar side chain T and S, the amino acid residues with an aromatic sidechain F, W or Y or the amino acid residues with a non-polar sidechain A, V, L, I and M may be substituted with one another.

The term "PBS" refers to phosphate-buffered saline containing 137 mM NaCl, 10 mM phosphate and 2.7 mM KCl and having a pH of 7.4.

The term "percent (%) sequence identity" with respect to a specific amino acid sequence (e.g. the amino acid sequence of a N-terminal capping module of the invention) is defined as the percentage of amino acid residues in a candidate sequence that is identical with the amino acid residues in the specific amino acid sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2 or ALIGN. Those skilled in the art can determine appropriate parameters for measuring alignment, including any algorithms needed to achieve maximal alignment over the full length of the sequences being compared. Further examples of how to determine the percentage of sequence identity can be found in WO 2009/058564 A2, page 93, line 14 to page 102, line 5.

The term "pharmaceutically acceptable carrier" refers to buffers, carriers, and other excipients suitable for use in contact with tissues of humans and/or animals without excessive toxicity, allergic response, irritation, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration.

The term "pharmaceutical composition" refers to a composition comprising at least one active agent and at least one pharmaceutically acceptable carrier. A pharmaceutical composition is generally formulated and administered to exert a pharmaceutically useful effect while minimizing undesirable side effects.

If the term "position" is used without further reference to a particular amino acid sequence, then it refers to the corresponding amino acid position of SEQ ID NO: 3. Furthermore, "corresponding" in this context means that the amino acid residue aligns with the indicated position of a specific sequence in a sequence alignment. Alignment for purposes of determining which amino acid residue corresponds to which position of a specific sequence can be achieved in various ways that are within the skill in the art, for instance, using publicly available computer software such as BLAST, BLAST-2 or ALIGN. Those skilled in the art can determine appropriate parameters for measuring alignment, including any algorithms needed to achieve maximal alignment over the full length of the sequences being compared. Further examples of how to align two sequences can be found in WO 2009/058564 A2, page 94, line 7 to page 96, line 28.

The term "recombinant", as used in reference to a protein, refers to a protein produced from a recombinant nucleic acid. A "recombinant nucleic acid" refers to nucleic acid molecules formed by laboratory methods of genetic recombination or gene synthesis.

The term "substantially identical", as used in reference to a specific amino acid sequence (e.g. the N-terminal capping module of the invention or an internal ankyrin repeat), refers to amino acid sequences having (1) at least 70%, at least 75%, at least 80%, at least 85%, at least 90%, at least 95%, or 100% sequence identity to the specific amino acid sequence or (2) up to 9, up to 8, up to 7, up to 6, up to 5, up to 4, up to 3, up to 2, up to 1 or no modifications, as compared to the specific amino acid sequence.

The term "target", as used, for instance, in conjunction with the specific binding property of an ankyrin repeat domain comprised in a protein, refers to any substance or structure. It may refer to a single molecule, such as a protein, small-molecule or sugar, as well as complexed molecules, such as interacting proteins or proteins binding to non-proteinaceous compounds. It may also refer to more macromolecular structures, such as cells, tissues, viruses or bacteria.

The terms "treating" or "treatment" of a disease, condition or symptom refers to obtaining therapeutic and/or prophylactic benefit, including alleviating, ablating, ameliorating, or preventing a disease, condition or symptoms, preventing additional symptoms, ameliorating or preventing the underlying metabolic causes of symptoms, inhibiting the disease or condition, e.g., arresting or slowing down the development of the disease or condition, relieving the disease or condition, causing regression of the disease or condition, relieving a condition caused by the disease or condition, or stopping the symptoms of the disease or condition.

Naturally occurring ankyrin repeat domains normally have capping modules to shield their hydrophobic cores from the solvent. In line with this, earlier developed recombinant proteins having ankyrin repeat domains likewise comprised capping modules with such a shielding function at the N- and C-terminal ends of the ankyrin repeat domain (e.g. Binz, 2003, loc. cit. and Binz, 2004, loc. cit.). The capping modules that were first used were derived from the murine GABPβ1, which is a naturally occurring ankyrin repeat protein (PDB: 1AWC_B). Binz et al. 2003 (loc. cit.) already introduced some modifications to the naturally occurring capping modules in order to adapt the capping modules for binding to the internal ankyrin repeats and for cloning purposes. The N-terminal capping module of Binz et al. 2003 (loc. cit.) is reflected by SEQ ID NO: 3 and the C-terminal capping module of Binz et al. 2003 (loc. cit.) is reflected by SEQ ID NO: 83.

WO 2012/069655 relates to further modified N-terminal and C-terminal capping modules of the ankyrin repeat domain. The N-terminal capping modules disclosed in WO 2012/069655 include the two N-terminal capping modules reflected by SEQ ID NO: 1 and SEQ ID NO: 2 (corresponding to SEQ ID NO: 15 and 14 of WO 2012/069655, respectively, without the two optionally missing N-terminal amino acid residues). Another exemplary N-terminal capping module disclosed in the prior art includes the one reflected by SEQ ID NO: 4 corresponding to an amino acid sequence comprised in the N-terminal capping module of SEQ ID NO: 56 of WO 2016/156596 A1.

Using in silico structure analysis, the present inventors determined those amino acid residues that would appear to be most suitable for each position of the N-terminal capping module of the ankyrin repeat domain. In particular, the various amino acid residues shown in Table 1 were considered to be particularly suitable based on the in silico analysis.

Based on the structural analysis, amino acid residues in various positions were tested by in vitro experimentation. Among the many tested mutations of the N-terminal capping module, there was one position which was surprisingly found to be particularly important for the thermostability of the ankyrin repeat domain—the position corresponding to position 15 of SEQ ID NO: 3 (also simply referred to as position 15 herein without referencing SEQ ID NO: 3).

Accordingly, the protein of the invention comprises an ankyrin repeat domain that has an N-terminal capping module with a mutation in position 15.

In some embodiments, the ankyrin repeat domain of the protein of the invention has improved properties, which may include improved thermostability, improved storage stability, improved thermodynamic stability (defined as the difference in free energy between the folded and unfolded states), improved folding and/or refolding properties (such as a higher fraction of refolded ankyrin repeat domains after thermal denaturation), reduced aggregation propensity and lower in vivo immunogenicity risk.

In some embodiments, the N-terminal capping module has an amino acid residue at position 15 selected from the group consisting of I, T, A, V, L, M, S, Q and R. In some embodiments, the N-terminal capping module has an amino acid residue at position 15 selected from the group consisting of I, T, A, V, L, M and S. In some embodiments, the N-terminal capping module has an amino acid residue at position 15 selected from the group consisting of I, T, A, V, L and M. In some embodiments, the N-terminal capping module has I at position 15. In some embodiments, the N-terminal capping module has T at position 15. In some embodiments, the N-terminal capping module has A at position 15. In some embodiments, the N-terminal capping module has V at position 15. In some embodiments, the N-terminal capping module has L at position 15. In some embodiments, the N-terminal capping module has M at position 15.

In some embodiments, the N-terminal capping module has, apart from the mutation in position 15, an amino acid residue of Table 1 in one or more of the other positions.

In some embodiments, the N-terminal capping module further has an amino acid residue at position 3 selected from the group consisting of G, A, D and S. In some embodiments, the N-terminal capping module has an amino acid residue at position 3 selected from A and S. In some embodiments, the N-terminal capping module has A at position 3. In some embodiments, the N-terminal capping module has S at position 3.

In some embodiments, the N-terminal capping module further has an amino acid residue at position 8 selected from the group consisting of E, D, Q, N, S, T, K and R. In some embodiments, the N-terminal capping module has Q at position 8.

In some embodiments, the N-terminal capping module further has an amino acid residue at position 11 selected from the group consisting of L, S, Q, K, R, A, H, D and E. In some embodiments, the N-terminal capping module has an amino acid residue at position 11 selected from K, E, Q, A and L. In some embodiments, the N-terminal capping module has A at position 11.

In some embodiments, the N-terminal capping module further has an amino acid residue at position 16 selected from the group consisting of D, A, N, Q, G, S, T, K, E and R. In some embodiments, the N-terminal capping module has E at position 16.

In some embodiments, the N-terminal capping module further has an amino acid residue at position 17 selected from the group consisting of D, A, N, Q, G, S, T, K, E and R. In some embodiments, the N-terminal capping module has A at position 17.

In some embodiments, the N-terminal capping module further has an amino acid residue at position 19 selected from the group consisting of R, E, D, K, A, N, Q, S, T and H. In some embodiments, the N-terminal capping module has E at position 19.

In some embodiments, the N-terminal capping module further has an amino acid residue at position 20 selected from the group consisting of I, V, N, K, R, T, S, E, Q, A, D and H. In some embodiments, the N-terminal capping module has Q at position 20.

In some embodiments, the N-terminal capping module further has an amino acid residue at position 22 selected from the group consisting of L, V, I and A. In some embodiments, the N-terminal capping module further has an amino acid residue at position 22 selected from the group consisting of L, V and I. In some embodiments, the N-terminal capping module has L at position 22. In some embodiments, the N-terminal capping module has V at position 22. In some embodiments, the N-terminal capping module has I at position 22. In some embodiments, the N-terminal capping module has A at position 22.

In some embodiments, the N-terminal capping module has L at position 15 and I at position 22. In some embodiments, the N-terminal capping module has M at position 15 and I at position 22. In some embodiments, the N-terminal capping module has T at position 15 and I at position 22. In some embodiments, the N-terminal capping module has I at position 15 and I at position 22. In some embodiments, the N-terminal capping module has A at position 15 and I at position 22. In some embodiments, the N-terminal capping module has V at position 15 and I at position 22.

In some embodiments, the N-terminal capping module has L at position 15 and L at position 22. In some embodiments, the N-terminal capping module has M at position 15 and L at position 22. In some embodiments, the N-terminal capping module has T at position 15 and L at position 22. In some embodiments, the N-terminal capping module has I at position 15 and L at position 22. In some embodiments, the N-terminal capping module has A at position 15 and L at position 22. In some embodiments, the N-terminal capping module has V at position 15 and L at position 22.

In some embodiments, the N-terminal capping module has L at position 15 and V at position 22. In some embodiments, the N-terminal capping module has M at position 15 and V at position 22. In some embodiments, the N-terminal capping module has T at position 15 and V at position 22. In some embodiments, the N-terminal capping module has I at position 15 and V at position 22. In some embodiments, the N-terminal capping module has A at position 15 and V at position 22. In some embodiments, the N-terminal capping module has V at position 15 and V at position 22.

In some embodiments, the ankyrin repeat domain of the protein of the invention has an improved thermostability, such as a higher melting temperature and/or a higher fraction of refolded ankyrin repeat domains after thermal denaturation, as compared to a reference ankyrin repeat domain having the same amino acid sequence except for the mutation in position 15 of the N-terminal capping module.

Methods for measuring the thermostability of a protein or a protein domain are well-known to the person skilled in the art. For instance, the thermostability can be measured by a thermal shift assay, differential scanning calorimetry and circular dichroism (CD). Another possible approach is to use differential scanning fluorimetry (e.g. Nielsen et al., 2007, Nat Protoc. 2, 9:2212-21). In this method, unfolding of the protein is measured with a fluorescent dye that binds to hydrophobic parts of the protein. As the protein unfolds, more hydrophobic parts become exposed causing an increase in fluorescence and vice versa. This method therefore allows to conveniently monitor the refolding properties of a protein and to determine its melting temperature, which corresponds to the midpoint of the fluorescence transition curve. The refolding properties and melting temperature of a protein can also be measured by CD spectroscopy, whereby the thermal melting curve of the protein is determined by measuring the CD signal at 222 nm. For purposes of measuring the thermostability, the protein may be dissolved in PBS. For example, the thermostability of a helical protein can be determined by measuring the CD signal of the protein at 222 nm while slowly heating the protein at a concentration of 0.01 mM in PBS pH 7.4 from 20° C. to 95° C. using a temperature ramp of 1° C. per min.

In some embodiments, the increase in melting temperature of the ankyrin repeat domain of the invention is at least 1° C., at least 2° C., at least 3° C., at least 4° C. or at least 5° C., as compared to the reference ankyrin repeat domain.

In some embodiments, the fraction of the refolded ankyrin repeat domains after thermal denaturation is at least 1%, at least 5%, at least 10% or at least 20% higher, as compared to the reference ankyrin repeat domain.

In some embodiments, the ankyrin repeat domain has a higher melting temperature and/or higher fraction of refolded ankyrin repeat domains after thermal denaturation. In some embodiments, the ankyrin repeat domain has a higher melting temperature and/or higher fraction of refolded ankyrin repeat domains after thermal denaturation than a reference ankyrin repeat domain with the same amino acid sequence except for position 15 of the N-terminal capping module that is a different amino acid residue in the reference ankyrin repeat domain compared to the ankyrin repeat domain of the protein of the invention. In some embodiments, the amino acid residue in position 15 of the reference ankyrin repeat domain is selected from the group consisting of E, D, G, H, K and N. In some embodiments, the amino acid residue in position 15 of the reference ankyrin repeat domain is E. In some embodiments, the amino acid residue in position 15 of the reference ankyrin repeat domain is D.

Unless specified, the sequence of the ankyrin repeat domain is not particularly limited. In particular, the ankyrin repeat domain allows for a large sequence variation while preserving the overall structure and function of the domain.

In some embodiments, the N-terminal capping module comprises an amino acid sequence that is substantially identical to an amino acid sequence selected from the group consisting of SEQ ID NOs: 1 to 76 and 110. In some embodiments, the N-terminal capping module comprises an amino acid sequence that is substantially identical to an amino acid sequence selected from the group consisting of SEQ ID NOs: 7 to 16. In some embodiments, the N-terminal capping module comprises an amino acid sequence that is substantially identical to an amino acid sequence selected from the group consisting of SEQ ID NOs: 17 to 26. In some embodiments, the N-terminal capping module comprises an amino acid sequence that is substantially identical to an amino acid sequence selected from the group consisting of SEQ ID NOs: 27 to 36. In some embodiments, the N-terminal capping module comprises an amino acid sequence that is substantially identical to an amino acid sequence selected from the group consisting of SEQ ID NOs: 37 to 46. In some embodiments, the N-terminal capping module comprises an amino acid sequence that is substantially identical to an amino acid sequence selected from the group consisting of SEQ ID NOs: 47 to 56. In some embodiments, the N-terminal capping module comprises an amino acid sequence that is substantially identical to an amino acid sequence selected from the group consisting of SEQ ID NOs: 57 to 66 and 110. In some embodiments, the N-terminal capping module comprises an amino acid sequence that is substantially identical to an amino acid sequence selected from the group consisting of SEQ ID NOs: 67 to 76.

In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 1 to 76 and 110. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 7 to 16. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 17 to 26. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 27 to 36. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 37 to 46. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 47 to 56. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 57 to 66 and 110. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 67 to 76.

In some embodiments, the N-terminal capping module comprises an amino acid sequence that is identical to an amino acid sequence selected from the group consisting of SEQ ID NOs: 7 to 76 and 110. In some embodiments, the N-terminal capping module comprises an amino acid sequence that is identical to an amino acid sequence selected from the group consisting of SEQ ID NOs: 7 to 16. In some embodiments, the N-terminal capping module comprises an amino acid sequence that is identical to an amino acid sequence selected from the group consisting of SEQ ID NOs: 17 to 26. In some embodiments, the N-terminal capping module comprises an amino acid sequence that is identical to an amino acid sequence selected from the group consisting of SEQ ID NOs: 27 to 36. In some embodiments, the N-terminal capping module comprises an amino acid sequence that is identical to an amino acid sequence selected from the group consisting of SEQ ID NOs: 37 to 46. In some embodiments, the N-terminal capping module comprises an amino acid sequence that is identical to an amino acid sequence selected from the group consisting of SEQ ID NOs: 47 to 56. In some embodiments, the N-terminal capping module comprises an amino acid sequence that is identical to an amino acid sequence selected from the group consisting of SEQ ID NOs: 57 to 66 and 110. In some embodiments, the N-terminal capping module comprises an amino acid sequence that is identical to an amino acid sequence selected from the group consisting of SEQ ID NOs: 67 to 76. In some embodiments, the N-terminal capping module comprises an amino acid sequence that is identical to SEQ ID NO: 110.

In some embodiments, the N-terminal capping module comprises an amino acid sequence selected from the group consisting of SEQ ID NOs: 7 to 16 or from a variant of any one of SEQ ID NOs: 7 to 16 with up to 9, up to 8, up to 7, up to 6, up to 5, up to 4, up to 3, up to 2 or up to 1 modifications outside position 15, and wherein X at position 15 of SEQ ID NOs: 7 to 16 or said variants thereof is an amino acid residue as defined above for position 15. In some embodiments, the variants of SEQ ID NOs: 7 to 16 have up to 9 modifications. In some embodiments, the variants of SEQ ID NOs: 7 to 16 have up to 8 modifications. In some embodiments, the variants of SEQ ID NOs: 7 to 16 have up to 7 modifications. In some embodiments, the variants of SEQ ID NOs: 7 to 16 have up to 6 modifications. In some embodiments, the variants of SEQ ID NOs: 7 to 16 have up to 5 modifications. In some embodiments, the variants of SEQ ID NOs: 7 to 16 have up to 4 modifications. In some embodiments, the variants of SEQ ID NOs: 7 to 16 have up to 3 modifications. In some embodiments, the variants of SEQ ID NOs: 7 to 16 have up to 2 modifications. In some embodiments, the variants of SEQ ID NOs: 7 to 16 have up to 1 modification. In some embodiments, there are no variants of SEQ ID NOs: 7 to 16. In some embodiments, the modifications of SEQ ID NOs: 7 to 16 do not include more than a combined number of deletions and insertions of 3. In some embodiments, the modifications of SEQ ID NOs: 7 to 16 do not include more than a combined number of deletions and insertions of 2. In some embodiments, the modifications of SEQ ID NOs: 7 to 16 do not include more than a combined number of deletions and insertions of 1. In some embodiments, the modifications of SEQ ID NOs: 7 to 16 are only substitutions. In some embodiments, the variants of SEQ ID NOs: 7 to 16 comprise one or more substitutions with an amino acid residue of Table 1.

In some embodiments, the N-terminal capping module comprises an amino acid sequence with amino acid residues as indicated for the positions 1 to 30 in Table 1. For instance, the amino acid residue at position 1 is selected from the group consisting of A, E, N, Q, G, S, T, K, D, R and H, and so on. In some embodiments, the N-terminal capping module comprises an amino acid sequence with amino acid residues as indicated for the positions 1 to 30 in Table 1 except for position 15 that is selected from the group consisting of I, T, A, V, L and M. In some embodiments, the N-terminal capping module comprises an amino acid sequence with amino acid residues as indicated for the positions 1 to 30 in Table 1 except for position 15 that is selected from the group consisting of I, T, A, V, L and M or a variant thereof with up to 9, up to 8, up to 7, up to 6, up to 5, up to 4, up to 3, up to 2 or up to 1 modifications outside position 15.

The N-terminal capping module may further comprise a sequence N-terminal to the amino acid sequences defined in SEQ ID NOs: 1 to 76 and 110 (or the sequence variants thereof defined herein). For instance, such sequence could be a dipeptide comprising amino acid residues selected from the group consisting of D, A, E, N, Q, S, T, K, R and H, such as the dipeptide GS, DA, EA, AA, AD, AE, NA, AN, PT, TP, AT or TA. In some embodiments, the dipeptide is directly N-terminal to the amino acid sequences defined in SEQ ID NOs: 1 to 76 and 110 (or the sequence variants thereof defined herein). Such dipeptide sequence primarily serves as a linker to connect the ankyrin repeat domain to the further peptide sequence of the protein or as an extended alpha-helix of the N-terminal capping module.

It is understood that for those embodiments of the N-terminal capping module, which are defined by a certain amino acid residue(s) in, e.g., position 15, as well as a minimal sequence identity to an amino acid sequence or a defined number of modifications compared to an amino acid sequence, both conditions need to be fulfilled. For instance, an N-terminal capping module having I in position 15 and at least 70% sequence identity to SEQ ID NOs: 7 to 16, only relates to such embodiments wherein the N-terminal capping module has I in position 15 and, at the same time, at least 70% sequence identity to one or more of SEQ ID NOs: 7 to 16.

In some embodiments, the internal ankyrin repeats of the ankyrin repeat domain consist of 33 amino acid residues.

In some embodiments, the internal ankyrin repeat(s) of the ankyrin repeat domain of the invention comprise an amino acid sequence that is substantially identical to an amino acid sequence selected from the group consisting of SEQ ID NOs: 77 to 82 or from the group consisting of SEQ ID NOs: 78 to 82. In some embodiments, the internal ankyrin repeat(s) comprise an amino acid sequence that has at least 70%, at least 75%, at least 80%, at least 85%, at least 90%, at least 95%, or 100% sequence identity to an amino acid sequence selected from the group consisting of SEQ ID NOs: 77 to 82 or from the group consisting of SEQ ID NOs: 78 to 82. In some embodiments, the internal ankyrin repeat(s) comprise an amino acid sequence selected from the group consisting of SEQ ID NOs: 77 to 82 or from a variant of any one of SEQ ID NOs: 77 to 82 with up to 9, up to 8, up to 7, up to 6, up to 5, up to 4, up to 3, up to 2 or up to 1 modifications. In some embodiments, the internal ankyrin repeat(s) comprise an amino acid sequence selected from the group consisting of SEQ ID NOs: 78 to 82 or from a variant of any one of SEQ ID NOs: 78 to 82 with up to 9, up to 8, up to 7, up to 6, up to 5, up to 4, up to 3, up to 2 or up to 1 modifications.

In some embodiments, the internal ankyrin repeat adjacent to the N-terminal capping module of the ankyrin repeat domain of the invention comprises an amino acid sequence that is substantially identical to an amino acid sequence selected from the group consisting of SEQ ID NOs: 77 to 82 or from the group consisting of SEQ ID NOs: 78 to 82. In some embodiments, the internal ankyrin repeat adjacent to the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 77 to 82 or from the group consisting of SEQ ID NOs: 78 to 82. In some embodiments, the internal ankyrin repeat adjacent to the N-terminal capping module comprises an amino acid sequence selected from the group consisting of SEQ ID NOs: 77 to 82 or from a variant of any one of SEQ ID NOs: 77 to 82 with up to 9, up to 8, up to 7, up to 6, up to 5, up to 4, up to 3, up to 2 or up to 1 modifications. In some embodiments, the internal ankyrin repeat adjacent to the N-terminal capping module comprises an amino acid sequence selected from the group consisting of SEQ ID NOs: 78 to 82 or from a variant of any one of SEQ ID NOs: 78 to 82 with up to 9, up to 8, up to 7, up to 6, up to 5, up to 4, up to 3, up to 2 or up to 1 modifications.

In some embodiments, the internal ankyrin repeats of an ankyrin repeat domain of the invention share a high degree of sequence identity or sequence similarity. In some embodiments, the internal ankyrin repeat(s) share at least 70%, at least 75%, at least 80%, at least 85%, at least 90% or at least 95% sequence identity.

In some embodiments, the C-terminal capping module of the ankyrin repeat domain of the invention comprises an amino acid sequence that is substantially identical to an amino acid sequence selected from the group consisting of SEQ ID NOs: 83 to 92, 111 and 112. In some embodiments, the C-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 83 to 92, 111 and 112. In some embodiments, the C-terminal capping module comprises an amino acid sequence selected from the group consisting of SEQ ID NOs: 83 to 92, 111 and 112 or from a variant of any one of SEQ ID NOs: 83 to 92, 111 and 112 with up to 9, up to 8, up to 7, up to 6, up to 5, up to 4, up to 3, up to 2 or up to 1 modifications.

In some embodiments, the N-terminal capping module of the ankyrin repeat domain of the invention comprises an amino acid sequence that is substantially identical to an amino acid sequence selected from the group consisting of SEQ ID NOs: 7 to 16 and the internal ankyrin repeat(s) comprise an amino acid sequence that is substantially identical to an amino acid sequence selected from the group consisting of SEQ ID NOs: 77 to 82. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 7 to 16 and the internal ankyrin repeat(s) comprise an amino acid sequence that has at least 70%, at least 75%, at least 80%, at least 85%, at least 90%, at least 95%, or 100% sequence identity to an amino acid sequence selected from the group consisting of SEQ ID NOs: 77 to 82. In some embodiments, the N-terminal capping module comprises an amino acid sequence that has at least 70% sequence identity to an amino acid sequence selected from the group consisting of SEQ ID NOs: 7 to 16 and the internal ankyrin repeat(s) comprise an amino acid sequence that has at least 70% sequence identity to an amino acid sequence selected from the group consisting of SEQ ID NOs: 77 to 82. In some embodiments, the N-terminal capping module comprises an amino acid sequence that has at least 75% sequence identity to an amino acid sequence selected from the group consisting of SEQ ID NOs: 7 to 16 and the internal ankyrin repeat(s) comprise an amino acid sequence that has at least 75% sequence identity to an amino acid sequence selected from the group consisting of SEQ ID NOs: 77 to 82. In some embodiments, the N-terminal capping module comprises an amino acid sequence that has at least 80% sequence identity to an amino acid sequence selected from the group consisting of SEQ ID NOs: 7 to 16 and the internal ankyrin repeat(s) comprise an amino acid sequence that has at least 80% sequence identity to an amino acid sequence selected from the group consisting of SEQ ID NOs: 77 to 82. In some embodiments, the N-terminal capping module comprises an amino acid sequence that has at least 85% sequence identity to an amino acid sequence selected from the group consisting of SEQ ID NOs: 7 to 16 and the internal ankyrin repeat(s) comprise an amino acid sequence that has at least 85% sequence identity to an amino acid sequence selected from the group consisting of SEQ ID NOs: 77 to 82. In some embodiments, the N-terminal capping module comprises an amino acid sequence that has at least 90% sequence identity to an amino acid sequence selected from the group consisting of SEQ ID NOs: 7 to 16 and the internal ankyrin repeat(s) comprise an amino acid sequence that has at least 90% sequence identity to an amino acid sequence selected from the group consisting of SEQ ID NOs: 77 to 82. In some embodiments, the N-terminal capping module comprises an amino acid sequence that has at least 95% sequence identity to an amino acid sequence selected from the group consisting of SEQ ID NOs: 7 to 16 and the internal ankyrin repeat(s) comprise an amino acid sequence that has at least 95% sequence identity to an amino acid sequence selected from the group consisting of SEQ ID NOs: 77 to 82. In some embodiments, the N-terminal capping module comprises an amino acid sequence that is identical to an amino acid sequence selected from the group consisting of SEQ ID NOs: 7 to 16 and the internal ankyrin repeat(s) comprise an amino acid sequence that is identical to an amino acid sequence selected from the group consisting of SEQ ID NOs: 77 to 82.

In some embodiments, the N-terminal capping module comprises an amino acid sequence that is substantially identical to an amino acid sequence selected from the group consisting of SEQ ID NOs: 7 to 16, the internal ankyrin repeat(s) comprise an amino acid sequence that is substantially identical to an amino acid sequence selected from the group consisting of SEQ ID NOs: 77 to 82, and the C-terminal capping module comprises an amino acid sequence that is substantially identical to an amino acid sequence selected from the group consisting of SEQ ID NOs: 83 to 92, 111 and 112. In some embodiments, the N-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 7 to 16, the internal ankyrin repeat(s) comprise an amino acid sequence that has at least 70%, at least 75%, at least 80%, at least 85%, at least 90%, at least 95%, or 100% sequence identity to an amino acid sequence selected from the group consisting of SEQ ID NOs: 77 to 82, and the C-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 83 to 92, 111 and 112. In some embodiments, the N-terminal capping module comprises an amino acid sequence that has at least 70% sequence identity to an amino acid sequence selected from the group consisting of SEQ ID NOs: 7 to 16, the internal ankyrin repeat(s) comprise an amino acid sequence that has at least 70% sequence identity to an amino acid sequence selected from the group consisting of SEQ ID NOs: 77 to 82, and the C-terminal capping module comprises an amino acid sequence that has at least 70% sequence identity to an amino acid sequence selected from the group consisting of SEQ ID NOs: 83 to 92, 111 and 112. In some embodiments, the N-terminal capping module comprises an amino acid sequence that has at least 75% sequence identity to an amino acid sequence selected from the group consisting of SEQ ID NOs: 7 to 16, the internal ankyrin repeat(s) comprise an amino acid sequence that has at least 75% sequence identity to an amino acid sequence selected from the group consisting of SEQ ID NOs: 77 to 82, and the C-terminal capping module comprises an amino acid sequence that has at least 75% sequence identity to an amino acid sequence selected from the group consisting of SEQ ID NOs: 83 to 92, 111 and 112. In some embodiments, the N-terminal capping module comprises an amino acid sequence that has at least 80% sequence identity to an amino acid sequence selected from the group consisting of SEQ ID NOs: 7 to 16, the internal ankyrin repeat(s) comprise an amino acid sequence that has at least 80% sequence identity to an amino acid sequence selected from the group consisting of SEQ ID NOs: 77 to 82, and the C-terminal capping module comprises an amino acid sequence that has at least 80% sequence identity to an amino acid sequence selected from the group consisting of SEQ ID NOs: 83 to 92, 111 and 112. In some embodiments, the N-terminal capping module comprises an amino acid sequence that has at least 85% sequence identity to an amino acid sequence selected from the group consisting of SEQ ID NOs: 7 to 16, the internal ankyrin repeat(s) comprise an amino acid sequence that has at least 85% sequence identity to an amino acid sequence selected from the group consisting of SEQ ID NOs: 77 to 82, and the C-terminal capping module comprises an amino acid sequence that has at least 85% sequence identity to an amino acid sequence selected from the group consisting of SEQ ID NOs: 83 to 92, 111 and 112. In some embodiments, the N-terminal capping module comprises an amino acid sequence that has at least 90% sequence identity to an amino acid sequence selected from the group consisting of SEQ ID NOs: 7 to 16, the internal ankyrin repeat(s) comprise an amino acid sequence that has at least 90% sequence identity to an amino acid sequence selected from the group consisting of SEQ ID NOs: 77 to 82, and the C-terminal capping module comprises an amino acid sequence that has at least 90% sequence identity to an amino acid sequence selected from the group consisting of SEQ ID NOs: 83 to 92, 111 and 112. In some embodiments, the N-terminal capping module comprises an amino acid sequence that has at least 95% sequence identity to an amino acid sequence selected from the group consisting of SEQ ID NOs: 7 to 16, the internal ankyrin repeat(s) comprise an amino acid sequence that has at least 95% sequence identity to an amino acid sequence selected from the group consisting of SEQ ID NOs: 77 to 82, and the C-terminal capping module comprises an amino acid sequence that has at least 95% sequence identity to an amino acid sequence selected from the group consisting of SEQ ID NOs: 83 to 92, 111 and 112. In some embodiments, the N-terminal capping module comprises an amino acid sequence that is identical to an amino acid sequence selected from the group consisting of SEQ ID NOs: 7 to 16, the internal ankyrin repeat(s) comprise an amino acid sequence that is identical to an amino acid sequence selected from the group consisting of SEQ ID NOs: 77 to 82, and the C-terminal capping module comprises an amino acid sequence that is identical to an amino acid sequence selected from the group consisting of SEQ ID NOs: 83 to 92, 111 and 112.

In some embodiments, the N-terminal capping module comprises an amino acid sequence selected from the group consisting of SEQ ID NOs: 7 to 16 or from a variant of any one of SEQ ID NOs: 7 to 16 with up to 9, up to 8, up to 7, up to 6, up to 5, up to 4, up to 3, up to 2 or up to 1 modifications outside position 15, and wherein X at position 15 of SEQ ID NOs: 7 to 16 or said variants thereof is an amino acid residue as defined above for position 15 and the internal ankyrin repeat(s) comprise an amino acid sequence that has at least 70%, at least 75%, at least 80%, at least 85%, at least 90%, at least 95%, or 100% sequence identity to an amino acid sequence selected from the group consisting of SEQ ID NOs: 77 to 82 or SEQ ID NOs: 78 to 82.

In some embodiments, the N-terminal capping module comprises an amino acid sequence selected from the group consisting of SEQ ID NOs: 7 to 16 or from a variant of any one of SEQ ID NOs: 7 to 16 with up to 9, up to 8, up to 7, up to 6, up to 5, up to 4, up to 3, up to 2 or up to 1 modifications outside position 15, and wherein X at position 15 of SEQ ID NOs: 7 to 16 or said variants thereof is an amino acid residue as defined above for position 15, the internal ankyrin repeat(s) comprise an amino acid sequence that has at least 70%, at least 75%, at least 80%, at least 85%, at least 90%, at least 95%, or 100% sequence identity to an amino acid sequence selected from the group consisting of SEQ ID NOs: 77 to 82 or SEQ ID NOs: 78 to 82, and the C-terminal capping module comprises an amino acid sequence that has at least 70%, at least 75%, at least 80%, at least 85%, at least 90%, at least 95%, or 100% sequence identity to an amino acid sequence selected from the group consisting of SEQ ID NOs: 83 to 92, 111 and 112.

In some embodiments, the ankyrin repeat domain comprises the N-terminal capping module, one internal ankyrin repeat and a C-terminal capping module (N1C). Such ankyrin repeat domains are shown in Example 1. In some embodiments, the ankyrin repeat domain comprises the N-terminal capping module, multiple internal ankyrin repeats and a C-terminal capping module. In one embodiment, the ankyrin repeat domain comprises the N-terminal capping module, 2 or 3 internal ankyrin repeats and a C-terminal capping module (N2C or N3C, respectively). In one embodiment, the ankyrin repeat domain is N2C. In another embodiment, the ankyrin repeat domain is N3C.

In some embodiments, the protein of the invention is a recombinant protein or DARPin.

In some embodiments, the ankyrin repeat domain of the protein of the invention specifically binds to a target. For instance, the ankyrin repeat domain may specifically bind to a mammalian serum albumin, such as human serum albumin.

The protein of the invention may comprise one or more further moieties in addition to the ankyrin repeat domain comprising the N-terminal capping module, such as a moiety binding to a target, a labeling moiety, a toxic moiety, a moiety improving the pharmacokinetics, a moiety providing effector functions, a moiety allowing for the purification of the protein or a moiety providing enzymatic activity. In some embodiments, the further moiety binding to a target is another ankyrin repeat domain, an antibody or fragment thereof or a receptor protein. In some embodiments, the further moiety binding to a target is another ankyrin repeat domain. In some embodiments, the labeling moiety is a stable isotope, a mass tag or a fluorescent label. In some embodiments, the toxic moiety is a chemotherapeutic agent, such as an alkylating agent, an antimetabolite, a taxane, or an anthracycline. In some embodiments, the moiety improving pharmacokinetics is a pegylation, a mammalian serum albumin, an immunoglobulin, a Fc domain of an immunoglobulin or a moiety binding to mammalian serum albumin or to an immunoglobulin. In one embodiment, the protein further contains an ankyrin repeat domain binding to a mammalian serum albumin. In some embodiments, the further moiety providing effector functions is a Fc domain of an immunoglobulin. In some embodiments, the moiety allowing for the purification of the protein is a FLAG-tag, a GST-tag, an HA-tag, a Myc-tag, a His-tag or a Strep-tag. In some embodiments, the further moiety providing enzymatic or fluorescence activity is, e.g., beta-lactamase or green fluorescence protein, respectively.

The further moiety may be proteinaceous or non-proteinaceous.

In some embodiments, the further moiety in addition to the ankyrin repeat domain comprising the N-terminal capping module is one or more additional ankyrin repeat domains. In some embodiments, the protein of the invention comprises more than one, e.g., at least two, at least three, at least four or at least five, ankyrin repeat domains. In some embodiments, the protein of the invention comprises more than one, e.g., at least two, at least three, at least four or at least five, ankyrin repeat domains each comprising the N-terminal capping module of the invention. In some embodiments, the protein of the invention comprises multiple ankyrin repeat domains which specifically bind to multiple targets. In some embodiments, the protein of the invention comprises a single ankyrin repeat domain.

The further moiety may connect covalently to the protein, for instance, via a peptide linker or via a maleimide-containing crosslinker. Suitable peptide linkers include glycine-serine linkers and proline-threonine linkers. In some embodiments, the peptide linkers have a length of 2 to 24 amino acid residues or 2 to 16 amino acid residues. Alternatively, the further moiety may connect non-covalently to the protein, for instance, via a multimerization moiety. In some embodiments, a multimerization moiety is an immunoglobulin heavy chain constant region, a leucine zipper or a free thiol which can form a disulfide bond with another free thiol.

In a further aspect, the present disclosure relates to a protein library of the proteins of the invention. At least two of these proteins of the protein library differ in the amino acid sequence of their ankyrin repeat domains. In some embodiments, the protein library has at least $10^3$, at least $10^5$, at least $10^7$, least $10^9$, least $10^{11}$ or at least $10^{13}$ proteins that differ in the amino acid sequence of the ankyrin repeat domain.

In some embodiments, the protein library comprises proteins of the invention having different ankyrin repeat domain structures. For instance, the protein library may contain a mixture of proteins with proteins having the N-terminal capping module, 2 internal ankyrin repeats and a C-terminal capping module and proteins having the N-terminal capping module, 3 internal ankyrin repeats and a C-terminal capping module. In some embodiments, the proteins of the protein library all share the same ankyrin repeat domain structure. For instance, the ankyrin repeat domain of all proteins of the library comprises the N-terminal capping module, 2 internal ankyrin repeats and a C-terminal capping module. In other embodiments, the ankyrin repeat domain of all proteins of the library comprises the N-terminal capping module, 3 internal ankyrin repeats and a C-terminal capping module. In some embodiments, the proteins of the library each comprise a single ankyrin repeat domain only.

The sequence variability in the ankyrin repeat domains of the protein library may be brought about randomly, e.g., by error-prone PCR of the nucleic acid molecules encoding the proteins, or it may be obtained by rational design followed by, e.g., direct synthesis of the nucleic acid molecules encoding the proteins ("design approach"). In some embodiments, the variability is introduced by the design approach. In the design approach, variability of the amino acid sequence is introduced in one or more than one position of the ankyrin repeat domains, which variable positions are also referred to as "randomized positions", i.e. those positions that can potentially be occupied by more than one amino acid residue, whereas the remaining positions remain unchanged and are also referred to as "fixed positions", i.e. those positions that are occupied by a specific amino acid residue. In some embodiments, the randomized positions are those positions occupied by potential target interaction residues and/or the fixed positions are those positions occupied by framework residues. In some embodiments, a subset of the positions occupied by potential target interaction residues are randomized positions. In some embodiments, all positions occupied by potential target interaction residues are randomized positions.

In certain embodiments, there are corresponding fixed positions and randomized positions in the different proteins of the protein library. Due to the intended variability in the randomized positions, the amino acid residues in each corresponding randomized position will usually differ, although there may also be identical amino acid residues in corresponding randomized positions for at least some of the proteins in the library (though, in such cases, the proteins will not necessarily have identical amino acid residues in each of their corresponding randomized positions). In some embodiments, the fixed positions and the randomized positions are the same for the ankyrin repeat domains of each protein of the protein library. In some embodiments wherein the ankyrin repeat domains have multiple internal ankyrin repeats, the internal ankyrin repeats of each ankyrin repeat domain have different randomized and fixed positions. In some embodiments wherein the ankyrin repeat domains have multiple internal ankyrin repeats, the internal ankyrin repeats of each ankyrin repeat domain have the same randomized and fixed positions.

The randomized positions may show different degrees of variability, i.e. they may potentially be occupied by a different set of amino acid residues. In some embodiments, the degree of variability differs between randomized positions. In some embodiments, the amino acid residue in a randomized position is any of the twenty natural amino acid residues. In some embodiments, a randomized position may only be occupied by a subset of the twenty natural amino acid residues. Such subsets can be those having common physicochemical properties, such as sets of hydrophobic, hydrophilic, acidic, basic, aromatic, or aliphatic amino acid residues. Other subsets are those comprising all twenty natural amino acid residues except for certain non-desired amino acid residues, such as sets not comprising cysteines or prolines. In yet other embodiments, the subsets comprise those amino acid residues that are found in the corresponding positions of naturally occurring ankyrin repeats.

In some embodiments, the proteins of the protein library share at least 70% sequence identity, at least 80% sequence identity, or at least 90% sequence identity in the amino acid sequence of their ankyrin repeat domains.

The above protein library can serve to select those proteins of the library that have a predetermined property, i.e. a certain property of interest that may be found in one of the proteins of the protein library and that can be screened for. Such predetermined property may include the specific binding to a target, the activation or inhibition of a target, such as an enzyme, and the blocking of an interaction between two targets. In some embodiments, the predetermined property is the specific binding to a target.

In one embodiment, the present disclosure provides a method for selecting a protein having a predetermined property, comprising the following steps:
 a) Providing a protein library of said proteins comprising an ankyrin repeat domain with the N-terminal capping module;
 b) Selecting a protein from the library having the predetermined property.

During the selection step b), the proteins can be selected using screening methods commonly known to the person skilled in the art, such as yeast display, protein fragment complementation assay, phage display or ribosome display. In some embodiments, the proteins are selected in step b) using phage display or ribosome display.

After the selection of a protein, the protein can be further modified, mutated and/or optimized by methods commonly known in the art.

For instance, amino acid sequence variants of the protein can be generated, e.g., by subjecting the nucleic acid encoding the selected protein to physical or chemical mutagens, copying said nucleic acid by error-prone PCR, using said nucleic acid for DNA shuffling or random chimeragenesis (Neylon C., Nucleic Acids Res., 32(4), 1448-1459, 2004). The protein library of such amino acid sequence variants may then again be subjected to the above selection step b) in order to select the variant(s) having the predetermined property.

The protein selected in step b) above may also be selectively mutated. For instance, one or more cysteine residues may be introduced, the thiol group(s) of which can then react with maleimide cross-linkers. Similarly, certain non-desirable amino acid residues may be removed, for instance, cysteines, which are prone to oxidations. Also, amino acid residues may be selectively mutated after analysis of the crystal structure so that the protein structure better fits to the target.

The protein selected in step b) may also become modified with the one or more further moieties in addition to the ankyrin repeat domain outlined above for the protein of the invention.

In further aspects, the present disclosure provides a nucleic acid encoding the protein of the invention, a vector comprising such nucleic acid and a cell or in vitro expression system comprising such nucleic acid or such vector.

The nucleic acid can be DNA or RNA, single stranded or double-stranded, in isolated form or part of a larger nucleic acid, e.g., of a vector or a chromosome. The nucleic acid may comprise elements that enable delivery of the nucleic acid to a cell and/or expression of the nucleic acid in a cell. For instance, the nucleic acid encoding the protein of the invention can be operatively linked to expression control sequences, which have an impact on the transcription and/or translation of the protein, such as promoters, enhancers, transcription terminators, start codons and stop codons. Depending on the intended application and/or context, the expression control sequences may be selected from any eukaryotic or prokaryotic organism. Suitable promoters may be constitutive or inducible promoters. Examples include the CMV-, lacZ-, T7-, T5-, RSV-, SV40-, AOX1-, and GAPDH-promoter. Suitable enhancers include the CMV-enhancer, insulin-responsive elements, and an SV40-enhancer. Transcription terminators include the SV40-, lacZ-, and tk-polyadenylation signal.

The present disclosure also provides a library with nucleic acid molecules encoding the protein of the invention. At least two of the nucleic acid molecules of the nucleic acid library differ in the nucleic acid sequence of their ankyrin repeat domains. In some embodiments, the nucleic acid library has at least $10^3$, at least $10^5$, at least $10^7$, or at least $10^9$ nucleic acid molecules that differ in the nucleic acid sequence coding for the ankyrin repeat domain.

The cell comprising the nucleic acid or vector encoding the protein of the invention can be a prokaryotic or a eukaryotic cell. In some embodiments, the cell is a bacterial, yeast or mammalian cell. In some embodiments, the cell is derived from *E. coli, P. pastoris, S. cerevisiae*, human, hamster or mouse. In some embodiments, the cell is selected from CHO, HEK293, BHK, NS0, Sp2/0, HT-1080, PER.C6, CAP and HuH-7 cells.

In some embodiments, the in vitro expression system comprising the nucleic acid or vector encoding the protein of the invention is based on a cell-free extract from *E. coli*, yeast, rabbit, wheat germ, insect or human.

In a further aspect, the present disclosure provides a method of preparing a protein comprising the following steps:
  a) culturing a cell comprising a nucleic acid encoding the protein of the invention under conditions allowing expression thereof; and
  b) purifying the expressed protein.

In one embodiment, the present disclosure provides a method of modifying an existing ankyrin repeat domain by replacing the N-terminal capping module of the existing ankyrin repeat domain by an N-terminal capping module disclosed herein. By modifying an existing ankyrin repeat domain in this way, the favorable properties related to the N-terminal capping module disclosed herein may be transferred to the existing ankyrin repeat domain.

Thus, in one embodiment, the present disclosure provides a method of preparing a protein comprising an ankyrin repeat domain with an improved thermostability, such as a higher melting temperature and/or higher fraction of refolded ankyrin repeat domains after thermal denaturation, comprising the following steps:
  a) selecting a protein comprising an ankyrin repeat domain;
  b) determining the amino acid sequence of the N-terminal capping module of said ankyrin repeat domain;
  c) substituting the amino acid residue in the position of the N-terminal capping module corresponding to position 15 of SEQ ID NO: 3 by an amino acid residue disclosed for position 15 for the protein of the invention herein; and wherein the thermostability of the resulting ankyrin repeat protein is improved in comparison to a reference ankyrin repeat domain having the same amino acid sequence except for the mutation(s) in position 15 of the N-terminal capping module.

For instance, the amino acid residue corresponding to position 15 of SEQ ID NO: 3 may be substituted by an amino acid residue selected from the group consisting of I, T, A, V, L and M.

Thus, in one embodiment, the present disclosure provides a method of preparing a protein comprising an ankyrin repeat domain with an improved thermostability, such as a higher melting temperature and/or higher fraction of refolded ankyrin repeat domains after thermal denaturation, comprising the following steps:
  a) selecting a protein comprising an ankyrin repeat domain having an amino acid residue which is none of I, T, A, V, L and M at the position of the N-terminal capping module corresponding to position 15 of SEQ ID NO: 3;
  b) substituting the amino acid residue in said position by an amino acid residue selected from the group consisting of I, T, A, V, L and M.

In one embodiment, the present disclosure provides a method of preparing a protein comprising the following steps:
  a) assembling by genetic means one or more gene(s) encoding the protein of the invention, wherein one gene comprises sequence encoding the ankyrin repeat domain that comprises the N-terminal capping module, followed by one or more internal ankyrin repeats and a C-terminal capping module, and
  b) expressing the gene(s) encoding the protein of the invention.

The present disclosure also provides a pharmaceutical composition comprising the protein of the invention. In some embodiments, the pharmaceutical composition comprises the protein of the invention and a pharmaceutically acceptable carrier.

In a further aspect, the present disclosure provides the use of the proteins of the invention in a method of treatment.

Further Embodiments

1. A protein comprising an ankyrin repeat domain with an N-terminal capping module, wherein the amino acid residue of said N-terminal capping module corresponding to position 15 in SEQ ID NO: 3 is selected from the group consisting of I, T, A, V, L, M, S, Q and R.
2. A protein comprising an ankyrin repeat domain with an N-terminal capping module, wherein the amino acid residue of said N-terminal capping module corresponding to position 15 in SEQ ID NO: 3 is selected from the group consisting of I, T, A, V, L, M and S.
3. A protein comprising an ankyrin repeat domain with an N-terminal capping module, wherein the amino acid residue of said N-terminal capping module corresponding to position 15 in SEQ ID NO: 3 is selected from the group consisting of I, T, A, V, L and M.
4. A protein comprising an ankyrin repeat domain with an N-terminal capping module, wherein the amino acid residue of said N-terminal capping module corresponding to position 15 in SEQ ID NO: 3 is selected from the group consisting of I, T, A, V, L and M and the amino acid residue of said N-terminal capping module corresponding to position 22 in SEQ ID NO: 3 is selected from the group consisting of L, I and V.
5. The protein according to any one of items 1 to 4, wherein said N-terminal capping module comprises an amino acid sequence that is substantially identical to an amino acid sequence selected from the group consisting of SEQ ID NOs: 7 to 16.
6. The protein according to any one of items 1 to 4, wherein said N-terminal capping module comprises an amino acid sequence that has at least 70% sequence identity to an amino acid sequence selected from the group consisting of SEQ ID NOs: 7 to 16.

7. The protein according to any one of items 1 to 4, wherein said N-terminal capping module comprises an amino acid sequence that has at least 75% sequence identity to an amino acid sequence selected from the group consisting of SEQ ID NOs: 7 to 16.
8. The protein according to any one of items 1 to 4, wherein said N-terminal capping module comprises an amino acid sequence that has at least 80% sequence identity to an amino acid sequence selected from the group consisting of SEQ ID NOs: 7 to 16.
9. The protein according to any one of items 1 to 4, wherein said N-terminal capping module comprises an amino acid sequence that has at least 85% sequence identity to an amino acid sequence selected from the group consisting of SEQ ID NOs: 7 to 16.
10. The protein according to any one of items 1 to 4, wherein said N-terminal capping module comprises an amino acid sequence that has at least 90% sequence identity to an amino acid sequence selected from the group consisting of SEQ ID NOs: 7 to 16.
11. The protein according to any one of items 1 to 4, wherein said N-terminal capping module comprises an amino acid sequence that has at least 95% sequence identity to an amino acid sequence selected from the group consisting of SEQ ID NOs: 7 to 16.
12. The protein according to any one of items 1 to 4, wherein said N-terminal capping module comprises an amino acid sequence that is identical to an amino acid sequence selected from the group consisting of SEQ ID NOs: 7 to 76 and 110.
13. A protein comprising an ankyrin repeat domain,
    wherein said ankyrin repeat domain comprises an N-terminal capping module having an amino acid sequence that has at least 70% sequence identity with an amino acid sequence selected from the group consisting of SEQ ID NOs: 7 to 16; and
    wherein the amino acid residue of said N-terminal capping module corresponding to position 15 in SEQ ID NO: 3 is selected from the group consisting of I, T, A, V, L and M.
14. A protein comprising an ankyrin repeat domain,
    wherein said ankyrin repeat domain comprises an N-terminal capping module having an amino acid sequence that has at least 75% sequence identity with an amino acid sequence selected from the group consisting of SEQ ID NOs: 7 to 16; and
    wherein the amino acid residue of said N-terminal capping module corresponding to position 15 in SEQ ID NO: 3 is selected from the group consisting of I, T, A, V, L and M.
15. A protein comprising an ankyrin repeat domain,
    wherein said ankyrin repeat domain comprises an N-terminal capping module having an amino acid sequence that has at least 80% sequence identity with an amino acid sequence selected from the group consisting of SEQ ID NOs: 7 to 16; and
    wherein the amino acid residue of said N-terminal capping module corresponding to position 15 in SEQ ID NO: 3 is selected from the group consisting of I, T, A, V, L and M.
16. A protein comprising an ankyrin repeat domain,
    wherein said ankyrin repeat domain comprises an N-terminal capping module having an amino acid sequence that has at least 85% sequence identity with an amino acid sequence selected from the group consisting of SEQ ID NOs: 7 to 16; and
    wherein the amino acid residue of said N-terminal capping module corresponding to position 15 in SEQ ID NO: 3 is selected from the group consisting of I, T, A, V, L and M.
17. A protein comprising an ankyrin repeat domain,
    wherein said ankyrin repeat domain comprises an N-terminal capping module having an amino acid sequence that has at least 90% sequence identity with an amino acid sequence selected from the group consisting of SEQ ID NOs: 7 to 16; and
    wherein the amino acid residue of said N-terminal capping module corresponding to position 15 in SEQ ID NO: 3 is selected from the group consisting of I, T, A, V, L and M.
18. A protein comprising an ankyrin repeat domain,
    wherein said ankyrin repeat domain comprises an N-terminal capping module having an amino acid sequence that has at least 95% sequence identity with an amino acid sequence selected from the group consisting of SEQ ID NOs: 7 to 16; and
    wherein the amino acid residue of said N-terminal capping module corresponding to position 15 in SEQ ID NO: 3 is selected from the group consisting of I, T, A, V, L and M.
19. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 9 modifications outside position 15; and
    wherein X at position 15 in SEQ ID NOs: 7 to 16 or said variants thereof is an amino acid residue selected from the group consisting of I, T, A, V, L and M.
20. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 8 modifications outside position 15; and
    wherein X at position 15 in SEQ ID NOs: 7 to 16 or said variants thereof is an amino acid residue selected from the group consisting of I, T, A, V, L and M.
21. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 6 modifications outside position 15; and
    wherein X at position 15 in SEQ ID NOs: 7 to 16 or said variants thereof is an amino acid residue selected from the group consisting of I, T, A, V, L and M.
22. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 4 modifications outside position 15; and wherein X at position 15 in SEQ ID NOs: 7 to 16 or said variants thereof is an amino acid residue selected from the group consisting of I, T, A, V, L and M.

23. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 2 modifications outside position 15; and
    wherein X at position 15 in SEQ ID NOs: 7 to 16 or said variants thereof is an amino acid residue selected from the group consisting of I, T, A, V, L and M.

24. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 1 modification outside position 15; and
    wherein X at position 15 in SEQ ID NOs: 7 to 16 or said variants thereof is an amino acid residue selected from the group consisting of I, T, A, V, L and M.

25. The protein according to any one of items 19 to 22, wherein the combined number of deletions and insertions of said variant of any one of SEQ ID NOs: 7 to 16 is not more than 3.

26. The protein according to any one of items 19 to 22, wherein the combined number of deletions and insertions of said variant of any one of SEQ ID NOs: 7 to 16 is not more than 2.

27. The protein according to any one of items 19 to 22, wherein the combined number of deletions and insertions of said variant of any one of SEQ ID NOs: 7 to 16 is not more than 1.

28. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 9 substitutions in other positions than position 15; and
    wherein X at position 15 in SEQ ID NOs: 7 to 16 or said variants thereof is an amino acid residue selected from the group consisting of I, T, A, V, L and M.

29. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 8 substitutions in other positions than position 15; and
    wherein X at position 15 in SEQ ID NOs: 7 to 16 or said variants thereof is an amino acid residue selected from the group consisting of I, T, A, V, L and M.

30. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 6 substitutions in other positions than position 15; and
    wherein X at position 15 in SEQ ID NOs: 7 to 16 or said variants thereof is an amino acid residue selected from the group consisting of I, T, A, V, L and M.

31. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 4 substitutions in other positions than position 15; and
    wherein X at position 15 in SEQ ID NOs: 7 to 16 or said variants thereof is an amino acid residue selected from the group consisting of I, T, A, V, L and M.

32. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 2 substitutions in other positions than position 15; and
    wherein X at position 15 in SEQ ID NOs: 7 to 16 or said variants thereof is an amino acid residue selected from the group consisting of I, T, A, V, L and M.

33. A protein comprising an ankyrin repeat domain,
    wherein said ankyrin repeat domain comprises an N-terminal capping module that has an amino acid sequence selected from the group consisting of SEQ ID NOs: 7 to 16 or from a variant of any one of SEQ ID NOs: 7 to 16 with up to 1 substitution in other positions than position 15; and
    wherein X at position 15 in SEQ ID NOs: 7 to 16 or said variants thereof is an amino acid residue selected from the group consisting of I, T, A, V, L and M.

34. A protein comprising an ankyrin repeat domain,
    wherein said ankyrin repeat domain comprises an N-terminal capping module having an amino acid sequence that has at least 70%, at least 75%, at least 80%, at least 85%, at least 90%, at least 95%, or 100% sequence identity with SEQ ID NO: 58, and
    wherein the amino acid residue of said N-terminal capping module corresponding to position 15 in SEQ ID NO: 3 is selected from the group consisting of I, T, A, V, L and M.

35. The protein according to any one of items 1 to 34, wherein said N-terminal capping module further has an amino acid residue selected from the group consisting of G, A, D and S at the position corresponding to position 3 in SEQ ID NO: 3.

36. The protein according to item 35, wherein said amino acid residue of the N-terminal capping module corresponding to position 3 in SEQ ID NO: 3 is A or S.

37. The protein according to any one of items 1 to 36, wherein said N-terminal capping module further has an amino acid residue selected from the group consisting of L, S, Q, K, R, A, H, D and E at the position corresponding to position 11 in SEQ ID NO: 3.

38. The protein according to item 37, wherein said amino acid residue of the N-terminal capping module corresponding to position 11 in SEQ ID NO: 3 is selected from the group consisting of K, E, Q, A and L.

39. The protein according to any one of items 1 to 38, wherein said N-terminal capping module further has an amino acid residue selected from the group consisting of D, A, N, Q, G, S, T, K, E and R at the position corresponding to position 17 in SEQ ID NO: 3.
40. The protein according to item 39, wherein said amino acid residue of the N-terminal capping module corresponding to position 17 in SEQ ID NO: 3 is A.
41. The protein according to any one of items 1 to 40, wherein said N-terminal capping module further has an amino acid residue selected from the group consisting of N, K, R, T, S, E, Q, A, D and H at the position corresponding to position 20 in SEQ ID NO: 3.
42. The protein according to item 41, wherein said amino acid residue of the N-terminal capping module corresponding to position 20 in SEQ ID NO: 3 is Q.
43. A protein comprising an ankyrin repeat domain with an N-terminal capping module, wherein the amino acid residue of said N-terminal capping module corresponding to position 15 in SEQ ID NO: 3 is selected from the group consisting of I, T, A, V, L and M, the amino acid residue of said N-terminal capping module corresponding to position 3 in SEQ ID NO: 3 is A or S, the amino acid residue of said N-terminal capping module corresponding to position 11 in SEQ ID NO: 3 is selected from the group consisting of K, E, Q, A and L, the amino acid residue of said N-terminal capping module corresponding to position 17 in SEQ ID NO: 3 is A and the amino acid residue of said N-terminal capping module corresponding to position 20 in SEQ ID NO: 3 is Q.
44. The protein according to any one of items 1 to 43, wherein said N-terminal capping module further has the amino acid residues G and S or D and A N-terminal to the amino acid sequence corresponding to SEQ ID NO: 3 at the positions corresponding to −2 and −1 of SEQ ID NO: 3, respectively.
45. The protein according to any one of items 1 to 44, wherein said N-terminal capping module is an N-terminal capping repeat.
46. The protein according to any one of items 1 to 45, wherein said ankyrin repeat domain has one or more internal ankyrin repeats, each consisting of 33 amino acid residues.
47. The protein according to any one of items 1 to 46, wherein said ankyrin repeat domain has two or three internal ankyrin repeats.
48. The protein according to any one of items 1 to 47, wherein said ankyrin repeat domain comprises one or more internal ankyrin repeats, and
   wherein said one or more internal ankyrin repeats each have an amino acid sequence having at least 70% sequence identity with an amino acid sequence selected from the group consisting of SEQ ID NOs: 77 to 82.
49. The protein according to any one of items 1 to 47, wherein said ankyrin repeat domain comprises one or more internal ankyrin repeats, and
   wherein said one or more internal ankyrin repeats each have an amino acid sequence that is substantially identical to an amino acid sequence selected from the group consisting of SEQ ID NOs: 77 to 82.
50. The protein according to any one of items 1 to 49, wherein said ankyrin repeat domain comprises one or more internal ankyrin repeats, and
   wherein said one or more internal ankyrin repeats each comprise an amino acid sequence selected from the group consisting of SEQ ID NOs: 77 to 82 or from a variant of any one of SEQ ID NOs: 77 to 82 with up to 9, up to 8, up to 7, up to 6, up to 5, up to 4, up to 3, up to 2 or up to 1 modifications.
51. The protein according to any one of items 1 to 49, wherein the internal ankyrin repeat of the ankyrin repeat domain that is adjacent to said N-terminal capping module comprises an amino acid sequence selected from the group consisting of SEQ ID NOs: 77 to 82 or from a variant of any one of SEQ ID NOs: 77 to 82 with up to 9, up to 8, up to 7, up to 6, up to 5, up to 4, up to 3, up to 2 or up to 1 modifications.
52. The protein according to any one of items 1 to 51, wherein said ankyrin repeat domain comprises more than one internal ankyrin repeat, and wherein said internal ankyrin repeats share at least 70% sequence identity.
53. The protein according to any one of items 1 to 52, wherein said ankyrin repeat domain further comprises a C-terminal capping module having at least 70% sequence identity with an amino acid sequence selected from the group consisting of SEQ ID NOs: 83 to 92, 111 and 112.
54. The protein according to any one of items 1 to 52, wherein said ankyrin repeat domain further comprises a C-terminal capping module having an amino acid sequence that is substantially identical to an amino acid sequence selected from the group consisting of SEQ ID NOs: 83 to 92, 111 and 112.
55. A protein comprising an ankyrin repeat domain, wherein said ankyrin repeat domain comprises an N-terminal capping module, one or more internal ankyrin repeats and a C-terminal capping module, wherein said N-terminal capping module has an amino acid sequence that has at least 70% sequence identity with an amino acid sequence selected from the group consisting of SEQ ID NOs: 7 to 16,
   wherein the amino acid residue of said N-terminal capping module corresponding to position 15 in SEQ ID NO: 3 is selected from the group consisting of L, M, I, T, A, V and S, and
   wherein said one or more internal ankyrin repeats each have an amino acid sequence that has at least 70% sequence identity with an amino acid sequence selected from the group consisting of SEQ ID NOs: 77 to 82.
56. A protein comprising an ankyrin repeat domain, wherein said ankyrin repeat domain comprises an N-terminal capping module, one or more internal ankyrin repeats and a C-terminal capping module,
   wherein said N-terminal capping module has an amino acid sequence that has at least 75% sequence identity with an amino acid sequence selected from the group consisting of SEQ ID NOs: 7 to 16,
   wherein the amino acid residue of said N-terminal capping module corresponding to position 15 in SEQ ID NO: 3 is selected from the group consisting of L, M, I, T, A, V and S, and
   wherein said one or more internal ankyrin repeats each have an amino acid sequence that has at least 75% sequence identity with an amino acid sequence selected from the group consisting of SEQ ID NOs: 77 to 82.
57. A protein comprising an ankyrin repeat domain, wherein said ankyrin repeat domain comprises an N-terminal capping module, one or more internal ankyrin repeats and a C-terminal capping module,
   wherein said N-terminal capping module has an amino acid sequence that has at least 80% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S, and
wherein said one or more internal ankyrin repeats each have an amino acid sequence that has at least 80% sequence identity with an amino acid sequence selected from the group consisting of SEQ ID NOs: 77 to 82.

58. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence that has at least 85% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S, and
wherein said one or more internal ankyrin repeats each have an amino acid sequence that has at least 85% sequence identity with an amino acid sequence selected from the group consisting of SEQ ID NOs: 77 to 82.

59. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence that has at least 90% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S, and
wherein said one or more internal ankyrin repeats each have an amino acid sequence that has at least 90% sequence identity with an amino acid sequence selected from the group consisting of SEQ ID NOs: 77 to 82.

60. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence that has at least 95% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S, and
wherein said one or more internal ankyrin repeats each have an amino acid sequence that has at least 95% sequence identity with an amino acid sequence selected from the group consisting of SEQ ID NOs: 77 to 82.

61. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S, and
wherein said one or more internal ankyrin repeats each have an amino acid sequence selected from the group consisting of SEQ ID NOs: 77 to 82.

62. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence that has at least 70% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S,
wherein said one or more internal ankyrin repeats each have an amino acid sequence that has at least 70% sequence identity with an amino acid sequence selected from the group consisting of SEQ ID NOs: 77 to 82, and
wherein said C-terminal capping module has an amino acid sequence that has at least 70% sequence identity with an amino acid sequence selected from the group consisting of SEQ ID NOs: 83 to 92, 111 and 112.

63. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence that has at least 75% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S,
wherein said one or more internal ankyrin repeats each have an amino acid sequence that has at least 75% sequence identity with an amino acid sequence selected from the group consisting of SEQ ID NOs: 77 to 82, and
wherein said C-terminal capping module has an amino acid sequence that has at least 75% sequence identity with an amino acid sequence selected from the group consisting of SEQ ID NOs: 83 to 92, 111 and 112.

64. A protein comprising an ankyrin repeat domain, wherein said ankyrin repeat domain comprises an N-terminal capping module, one or more internal ankyrin repeats and a C-terminal capping module,
wherein said N-terminal capping module has an amino acid sequence that has at least 80% sequence identity with an amino acid sequence selected from the group consisting of SEQ ID NOs: 7 to 16,
wherein the amino acid residue of said N-terminal capping module corresponding to position 15 in SEQ ID NO: 3 is selected from the group consisting of L, M, I, T, A, V and S,
wherein said one or more internal ankyrin repeats each have an amino acid sequence that has at least 80% sequence identity with an amino acid sequence selected from the group consisting of SEQ ID NOs: 77 to 82, and wherein said C-terminal capping module has an amino acid sequence that has at least 80% sequence identity with an amino acid sequence selected from the group consisting of SEQ ID NOs: 83 to 92, 111 and 112.

65. A protein comprising an ankyrin repeat domain, wherein said ankyrin repeat domain comprises an N-terminal capping module, one or more internal ankyrin repeats and a C-terminal capping module, wherein said N-terminal capping module has an amino acid sequence that has at least 85% sequence identity with an amino acid sequence selected from the group consisting of SEQ ID NOs: 7 to 16, wherein the amino acid residue of said N-terminal capping module corresponding to position 15 in SEQ ID NO: 3 is selected from the group consisting of L, M, I, T, A, V and S, wherein said one or more internal ankyrin repeats each have an amino acid sequence that has at least 85% sequence identity with an amino acid sequence selected from the group consisting of SEQ ID NOs: 77 to 82, and wherein said C-terminal capping module has an amino acid sequence that has at least 85% sequence identity with an amino acid sequence selected from the group consisting of SEQ ID NOs: 83 to 92, 111 and 112.

66. A protein comprising an ankyrin repeat domain, wherein said ankyrin repeat domain comprises an N-terminal capping module, one or more internal ankyrin repeats and a C-terminal capping module, wherein said N-terminal capping module has an amino acid sequence that has at least 90% sequence identity with an amino acid sequence selected from the group consisting of SEQ ID NOs: 7 to 16, wherein the amino acid residue of said N-terminal capping module corresponding to position 15 in SEQ ID NO: 3 is selected from the group consisting of L, M, I, T, A, V and S, wherein said one or more internal ankyrin repeats each have an amino acid sequence that has at least 90% sequence identity with an amino acid sequence selected from the group consisting of SEQ ID NOs: 77 to 82, and wherein said C-terminal capping module has an amino acid sequence that has at least 90% sequence identity with an amino acid sequence selected from the group consisting of SEQ ID NOs: 83 to 92, 111 and 112.

67. A protein comprising an ankyrin repeat domain, wherein said ankyrin repeat domain comprises an N-terminal capping module, one or more internal ankyrin repeats and a C-terminal capping module, wherein said N-terminal capping module has an amino acid sequence that has at least 95% sequence identity with an amino acid sequence selected from the group consisting of SEQ ID NOs: 7 to 16, wherein the amino acid residue of said N-terminal capping module corresponding to position 15 in SEQ ID NO: 3 is selected from the group consisting of L, M, I, T, A, V and S, wherein said one or more internal ankyrin repeats each have an amino acid sequence that has at least 95% sequence identity with an amino acid sequence selected from the group consisting of SEQ ID NOs: 77 to 82, and wherein said C-terminal capping module has an amino acid sequence that has at least 95% sequence identity with an amino acid sequence selected from the group consisting of SEQ ID NOs: 83 to 92, 111 and 112.

68. A protein comprising an ankyrin repeat domain, wherein said ankyrin repeat domain comprises an N-terminal capping module, one or more internal ankyrin repeats and a C-terminal capping module, wherein said N-terminal capping module has an amino acid sequence selected from the group consisting of SEQ ID NOs: 7 to 16, wherein the amino acid residue of said N-terminal capping module corresponding to position 15 in SEQ ID NO: 3 is selected from the group consisting of L, M, I, T, A, V and S, wherein said one or more internal ankyrin repeats each have an amino acid sequence selected from the group consisting of SEQ ID NOs: 77 to 82, and wherein said C-terminal capping module has an amino acid sequence selected from the group consisting of SEQ ID NOs: 83 to 92, 111 and 112.

69. The protein according to any one of items 1 to 68, wherein said ankyrin repeat domain has a higher melting temperature than a reference ankyrin repeat domain having the same amino acid sequence except for the amino acid residue of the N-terminal capping module corresponding to position 15 in SEQ ID NO: 3, which is selected from the group consisting of E, D, G, H, K and N in the reference ankyrin repeat domain.

70. The protein according to any one of items 1 to 68, wherein said ankyrin repeat domain has a higher melting temperature than a reference ankyrin repeat domain having the same amino acid sequence except for the amino acid residue of the N-terminal capping module corresponding to position 15 in SEQ ID NO: 3, which is D in the reference ankyrin repeat domain.

71. The protein according to any one of items 1 to 68, wherein said ankyrin repeat domain has a higher melting temperature than a reference ankyrin repeat domain having the same amino acid sequence except for the amino acid residue of the N-terminal capping module corresponding to position 15 in SEQ ID NO: 3, which is E in the reference ankyrin repeat domain.

72. The protein according to any one of items 1 to 71, wherein said protein is a recombinant protein.

73. The protein according to any one of items 1 to 72, wherein said ankyrin repeat domain specifically binds to a target.

74. The protein according to item 73, wherein said target is a virus.

75. The protein according to any one of items 1 to 74, wherein said protein comprises one or more further moieties in addition to said ankyrin repeat domain.

76. The protein according to item 75, wherein said protein comprises one or more additional ankyrin repeat domains as further moieties.

77. The protein according to item 76, wherein all of said ankyrin repeat domains comprise the same N-terminal capping module.

78. The protein according to item 76 or 77, wherein said protein comprises one or more additional ankyrin repeat domains as further moieties that are connected by a proline-threonine linker.

79. The protein according to item 78, wherein the proline-threonine linker has a length of 2 to 24 amino acid residues.

80. The protein according to any one of items 1 to 79, wherein said protein comprises at least five ankyrin repeat domains.
81. The protein according to any one of items 1 to 75, wherein said protein only comprises a single ankyrin repeat domain.
82. A protein library comprising more than one protein according to any one of items 1 to 81.
83. The protein library according to item 82, wherein said library comprises at least $10^7$ proteins according to any one of items 1 to 81, wherein said proteins all differ in the amino acid sequence of their ankyrin repeat domain.
84. The protein library according to item 82 or 83, wherein the one or more proteins according to any one of items 1 to 81 share at least 70% sequence identity in their ankyrin repeat domain.
85. A method for selecting a protein having a predetermined property comprising the following steps:
    a. providing the protein library of any one of items 82 to 84;
    b. selecting a protein having the predetermined property from the protein library.
86. A method for selecting a protein having binding specificity to a target comprising the following steps:
    a. providing the protein library of any one of items 82 to 84;
    b. selecting a protein having binding specificity to the target from the protein library.
87. The method according to item 85 or 86, comprising:
    c. Further modifying the amino acid sequence of said selected protein.
88. A nucleic acid molecule comprising a sequence encoding the protein according to any one of items 1 to 81.
89. The nucleic acid molecule according to item 88, wherein the nucleic acid molecule is a vector or a chromosome.
90. A nucleic acid library comprising more than one nucleic acid molecule according to item 88.
91. A cell comprising the nucleic acid molecule according to item 88 or 89.
92. A method of preparing a protein comprising the following steps:
    a. culturing a cell comprising a nucleic acid encoding a protein according to any one of items 1 to 81 under conditions allowing expression of said protein; and
    b. purifying the expressed protein.
93. A method of preparing a protein comprising an ankyrin repeat domain with an improved thermostability comprising the following steps:
    a. selecting a protein comprising an ankyrin repeat domain,
    b. determining the amino acid sequence of the N-terminal capping module of said ankyrin repeat domain; and
    c. substituting the amino acid residue of said N-terminal capping module corresponding to position 15 of SEQ ID NO: 3 by an amino acid residue selected from the group consisting of I, T, A, V, L and M.
94. A method of preparing a protein comprising an ankyrin repeat domain with an improved thermostability comprising the following steps:
    a. selecting a protein comprising an ankyrin repeat domain having an amino acid residue which is none of I, T, A, V, L and M at the position of the N-terminal capping module corresponding to position 15 of SEQ ID NO: 3; and
    b. substituting the amino acid residue in said position by an amino acid residue selected from the group consisting of I, T, A, V, L and M.
95. The method of item 93 or 94 comprising the further step of substituting the amino acid residue of said N-terminal capping module corresponding to position 22 by an amino acid selected from the group consisting of L, I and V.
96. A pharmaceutical composition comprising a protein according to any one of items 1 to 81 and a pharmaceutically acceptable carrier.
97. A protein according to any one of items 1 to 81 for use in a method of treatment.
98. Use of a protein according to any one of items 1 to 81 for the manufacture of a medicament.
99. A method of treatment comprising administering the protein according to any one of items 1 to 81 to a subject.

EXAMPLES

Example 1: Effect of Mutations in the N-Terminal Capping Module on the Thermostability of the Ankyrin Repeat Domain Based on crystal structure data, each position of the N-terminal capping module of an ankyrin repeat domain was analyzed and predictions were made about the most suitable amino acid residues for each position. In light of the inherent difficulty to correctly predict the role of the mutations in the N-terminal capping module, various mutations were tested by in vitro experimentation.

Materials and Methods

Protein Sequences

Amongst others, His-tagged ankyrin repeat domains P #93 to P #109 corresponding to SEQ ID NOs: 93 to 109, respectively, were tested.

The DNA sequence encoding each ankyrin repeat domain was chemically synthesized and cloned into pQIq (Simon M. et al., Bioconjug Chem., 23(2), 279-86, 2012) expression vectors by standard techniques.

Protein Expression

The ankyrin repeat domains were expressed in *E. coli* BL21 or XL1-Blue cells and purified using their His-tag using standard protocols known to the person skilled in the art. Briefly, 25 ml of stationary overnight cultures (LB, 1% glucose, 100 mg/l of ampicillin; 37° C.) were used to inoculate 1 l cultures (same medium). At an absorbance of about 1 at 600 nm, the cultures were induced with 0.5 mM IPTG and incubated at 37° C. for 4 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. The ankyrin repeat domains were purified over a Ni-nitrilotriacetic acid column (2.5 ml column volume) according to the manufacturer's instructions (QIAgen, Germany). Up to 200 mg of highly soluble ankyrin repeat domains were purified from one liter of *E. coli* culture with a purity>95% as estimated from SDS-15% PAGE. Such purified ankyrin repeat domains were used for further characterizations.

CD Measurement

The CD signal of the ankyrin repeat domains was recorded at 222 nm in a Jasco J-810 instrument (Jasco, Japan) while slowly heating the ankyrin repeat domains at a concentration of 0.01 mM in PBS pH 7.4 from 20° C. to 95° C. using a temperature ramp of 1° C. per min. This is an effective means to follow the denaturation of ankyrin repeat domains as they mainly consist of alpha helices that show a strong change in their CD signal at 222 nm upon unfolding. The midpoint of the observed transition of such a measured CD signal trace for an ankyrin repeat domain corresponds to its Tm value. Tm values were derived as described in V. Consalvi et al. (*Protein Eng Des Sel.* 13, 501-507, 2000).

Results and Discussion

The melting curves for the above-mentioned ankyrin repeat domains were determined. Based on the measured melting curves, the Tm values of the various constructs were determined as described above.

Figure 1:
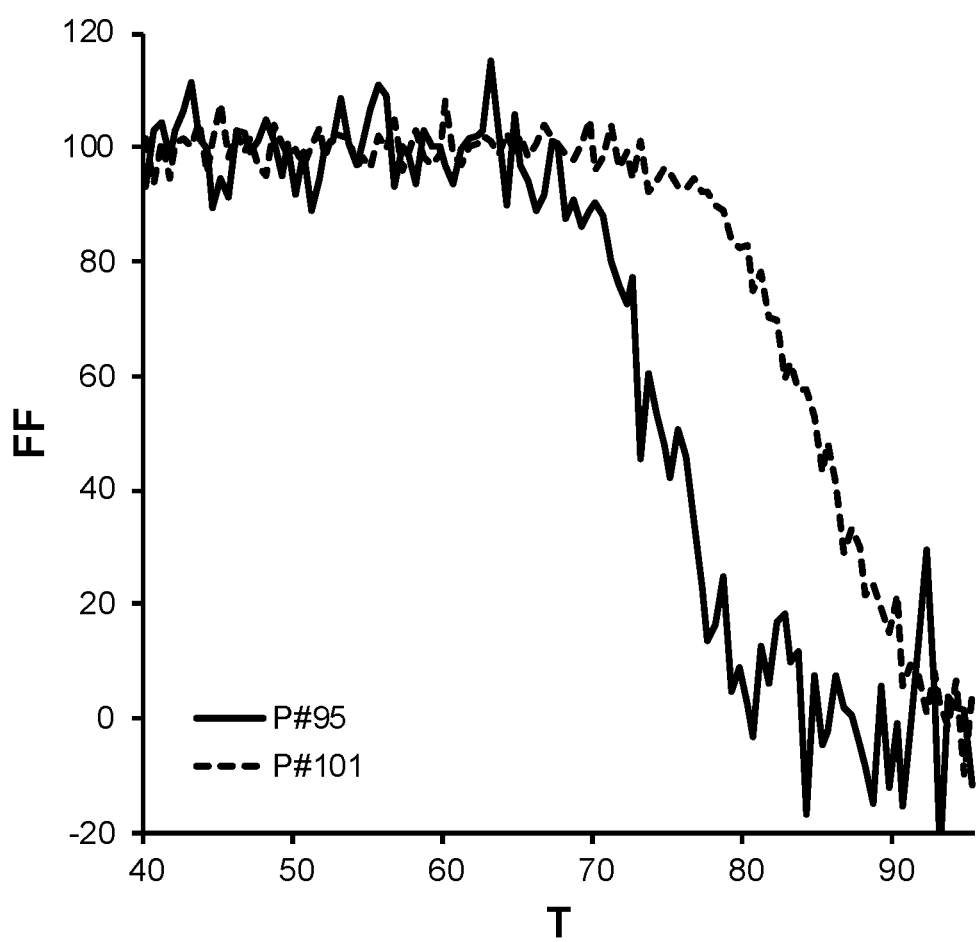
FIG. 1: Thermal stability of the designed ankyrin repeat proteins P #95 and P #101. Traces from thermal denaturation of proteins P #95 and P #101 are shown. The thermal denaturation is followed by the CD signal at 222 nm in PBS at pH 7.4. The Tm values for P #95 and P #101 were estimated to be 74.5° C. and 85.1° C., respectively.

The ankyrin repeat domain P #95 corresponding to SEQ ID NO: 95 was used as a first exemplary reference ankyrin repeat domain. P #95 comprises a D at position 27 (which corresponds to position 15 of its N-terminal capping module). P #96 to P #107 corresponding to SEQ ID NOs: 96 to 107, respectively, only differ in the amino acid residue at this position 15 of their N-terminal capping module from P #95. FIG. 1 shows, as an example, the melting curves of P #95 and P #101. Thus, changing a single amino acid at position 15 (from D to V) resulted in a strong increase of the Tm value of the ankyrin repeat protein of about 10° C. (the Tm values for P #95 and P #101 were estimated to be 74.5° C. and 85.1° C., respectively). Table 2 shows the Tm values and the corresponding amino acids at position 15 of the respective N-terminal capping modules of P #95 to P #107.

TABLE 2

| Protein | SEQ ID NO: | Position 15 | Tm value [° C.] |
|---|---|---|---|
| P#95 | 95 | D | 74.5 |
| P#96 | 96 | L | 84.6 |
| P#97 | 97 | M | 83.8 |
| P#98 | 98 | I | 84.8 |
| P#99 | 99 | T | 82.3 |
| P#100 | 100 | A | 82.4 |
| P#101 | 101 | V | 85.1 |
| P#102 | 102 | S | 79.3 |
| P#103 | 103 | N | 75.2 |
| P#104 | 104 | Q | 77.4 |
| P#105 | 105 | K | 77.9 |
| P#106 | 106 | R | 78.3 |
| P#107 | 107 | E | 79.2 |

Only some of the amino acid residues in position 15, in particular I, T, A, V, L and M resulted in a profound increase of the Tm value for the ankyrin repeat protein, e.g. when compared to D in this position 15.

A further reference ankyrin repeat domain (P #93) that was tested corresponds to SEQ ID NO: 93. P #93 comprises a D at position 27 (which corresponds to position 15 of its N-terminal capping module). The ankyrin repeat domain P #94 corresponding to SEQ ID NO: 94 is identical to P #93, with the exception that it contains the amino acid L at this position 15. FIG. 2 shows the melting curves of P #93 and P #94. Thus, changing a single amino acid at position 15 (from D to L) resulted in a strong increase of the Tm value of the ankyrin repeat protein of about 13° C. (the Tm values for P #93 and P #94 were estimated to be 62.1° C. and 75.2° C., respectively).

Yet another reference ankyrin repeat domain (P #108) that was tested corresponds to SEQ ID NO: 108. P #108 comprises a D at position 27 (which corresponds to position 15 of its N-terminal capping module). The ankyrin repeat domain P #109 corresponding to SEQ ID NO: 109 is identical to P #108, with the exception that it contains the amino acid L at this position 15. FIG. 3 shows the melting curves of P #108 and P #109. Thus, changing a single amino acid at position 15 (from D to L) resulted in a strong increase of the Tm value of the ankyrin repeat protein of about 14° C. (the Tm values for P #108 and P #109 were estimated to be 68.6° C. and 82.8° C., respectively).

Even though all three reference ankyrin repeat domains used (i.e. P #93, P #95 and P #109) significantly differ in their amino acid sequences of their N-terminal capping module (up to 9 amino acid differences outside position 15) a single mutation at position 15 can result in a surprisingly strong Tm increase of over 10° C. of the respective ankyrin repeat domain.

Overall, these data show that mutations at position 15 of a N-terminal capping module, in particular I, T, A, V, L and M, are beneficial for the thermostability of ankyrin repeat domains, incl. designed ankyrin repeat proteins or DARPins.

The stabilizing effect of such mutations in position 15 of the N-terminal capping module were further confirmed using different ankyrin repeat domains.

Example 2: Effect of Mutations in the N-Terminal Capping Module on the Thermostability of the Ankyrin Repeat Domain To confirm the stabilizing effect of the mutations in the N-terminal capping module, the mutations were tested in the context of further ankyrin repeat proteins.

Materials and Methods

Protein Sequences and Expression

His-tagged ankyrin repeat domains P #113 to P #125 corresponding to SEQ ID NOs: 113 to 125, respectively, were tested.

Cloning and expression of the ankyrin repeat domains was done as described in Example 1.

CD Measurement

The CD measurements of the ankyrin repeat domains P #122 to P #125 were done as described in Example 1.

The CD signal of the ankyrin repeat domains P #113 to P #121 was recorded at 222 nm in a Chirascan V100 instrument (Applied Photophysics) while slowly heating the ankyrin repeat domains at a concentration of 0.01 mM in PBS, 2M GdmCl, pH 7.4 from 25° C. to 100° C. using a temperature ramp of 1° C. per min, collecting data periodically at 0.5° C. intervals. Tm values were derived from the CD signal as described in Example 1.

Results and Discussion

The mutations at position 15 were transferred to three ankyrin repeat domains with different binding specificities and largely diverging sequences. In particular, the ankyrin repeat domain P #113 corresponding to SEQ ID NO: 113 specifically binds to human serum albumin (HSA), the ankyrin repeat domain P #116 corresponding to SEQ ID NO: 116 specifically binds to human vascular endothelial growth factor (VEGF) and the ankyrin repeat domain P #119 corresponding to SEQ ID NO: 119 specifically binds to human epidermal growth factor receptor 2 (HER2). In each of these ankyrin repeat domains, the D at position 27 of the respective sequences (which corresponds to position 15 in the N-terminal capping module) was replaced by V and L, respectively.

The Tm values of these ankyrin repeat domains are summarized in Table 3:

TABLE 3

| Protein | SEQ ID NO: | Target | Position 15 | Tm value [° C.] |
|---|---|---|---|---|
| P#113 | 113 | HSA | D | 76.0 |
| P#114 | 114 | HSA | L | 84.1 |
| P#115 | 115 | HSA | V | 81.9 |
| P#116 | 116 | VEGF | D | unfolded at RT of about 22° C. |
| P#117 | 117 | VEGF | L | 45.1 |
| P#118 | 118 | VEGF | V | 42 |
| P#119 | 119 | HER2 | D | 39.6 |
| P#120 | 120 | HER2 | L | 55.7 |
| P#121 | 121 | HER2 | V | 52.6 |

As reflected by the above table, replacing the amino acid residue at position 15 of the N-terminal capping module by either of V or L increases the thermostability of the ankyrin repeat domain in all tested backgrounds significantly.

The particular suitability of the mutations at position 15 of the N-terminal capping module was further confirmed in different ankyrin repeat domain backgrounds, including ankyrin repeat domain P #122 corresponding to SEQ ID NO: 122 (Tm of 83.7° C.), ankyrin repeat domain P #123 corresponding to SEQ ID NO: 123 (Tm of 83.9° C.), ankyrin repeat domain P #124 corresponding to SEQ ID NO: 124 (Tm of 81.7° C.) and ankyrin repeat domain P #125 corresponding to SEQ ID NO: 125 (Tm of 84.2° C.).

The invention claimed is:

1. A method of preparing a protein comprising an ankyrin repeat domain with an improved thermostability, the method comprising the following steps (A) or (B):
    (A) (i) providing a library with more than one protein, each protein comprising an ankyrin repeat domain that comprises an N-terminal capping module, one or more internal ankyrin repeat(s) and a C-terminal capping module,
    and
    (ii) selecting a protein having binding specificity to a target from the library of proteins of step (i), wherein the N-terminal capping module of the ankyrin repeat domain of said selected protein has an amino acid residue selected from the group consisting of I, T, A, V, L and M at the position corresponding to position 15 of SEQ ID NO: 58 and comprises an amino acid sequence that has at least 80% sequence identity with the amino acid sequence of SEQ ID NO: 58, and
    wherein the thermostability of the ankyrin repeat domain of said selected protein is improved in comparison to a reference ankyrin repeat domain having the same amino acid sequence except for the amino acid residue at the position of the N-terminal capping module corresponding to position 15 of SEQ ID NO: 58, which is D in the reference ankyrin repeat domain;
    or alternatively,
    (B) (i) selecting a protein comprising an ankyrin repeat domain that comprises an N-terminal capping module, one or more internal ankyrin repeat(s) and a C-terminal capping module, and
    (ii) replacing the N-terminal capping module of said ankyrin repeat domain by an N-terminal capping module that has an amino acid residue selected from the group consisting of I, T, A, V, L and M at the position corresponding to position 15 of SEQ ID NO: 58 and comprises an amino acid sequence that has at least 80% sequence identity with the amino acid sequence of SEQ ID NO: 58,
    wherein the thermostability of said ankyrin repeat domain with the replaced N-terminal capping module is improved in comparison to a reference ankyrin repeat domain having the same amino acid sequence except for the amino acid residue at the position of the N-terminal capping module corresponding to position 15 of SEQ ID NO: 58, which is D in the reference ankyrin repeat domain.

2. The method according to claim 1, wherein the N-terminal capping module of the ankyrin repeat domain of said selected protein according to the method of claim 1 (A) or the N-terminal capping module of said ankyrin repeat domain with the replaced N-terminal capping module according to the method of claim 1 (B) comprises an amino acid sequence has at least 90% sequence identity with the amino acid sequence of SEQ ID NO: 58.

3. The method according to claim 1, wherein the N-terminal capping module of the ankyrin repeat domain of said selected protein according to the method of claim 1 (A) or the N-terminal capping module of said ankyrin repeat domain with the replaced N-terminal capping module according to the method of claim 1 (B) comprises an amino acid sequence has at least 95% sequence identity with the amino acid sequence of SEQ ID NO: 58.

4. The method according to claim 3, wherein the N-terminal capping module of the ankyrin repeat domain of said selected protein according to the method of claim 1 (A) or the N-terminal capping module of said ankyrin repeat domain with the replaced N-terminal capping module according to the method of claim 1 (B) has L at the position corresponding to position 15 and a dipeptide GS to N-terminal to the sequence having the at least 95% sequence identity with the amino acid sequence of SEQ ID NO: 58; and
    wherein said ankyrin repeat domain of said selected protein according to the method of claim 1 (A) or said ankyrin repeat domain with the replaced N-terminal capping module according to the method of claim 1 (B) comprises one or more internal ankyrin repeats that each have an amino acid sequence having at least 95% sequence identity with the amino acid sequence of SEQ ID NO: 81.

5. The method according to claim 1, the method comprising the step (A).

6. The method according to claim 1, the method comprising the step (B).

7. The method according to claim 1 (A), wherein the protein selected in step b) is further modified with one or more ankyrin repeat domains.

8. The method according to claim 7, wherein the modified protein comprises at least five ankyrin repeat domains.

9. The method according to claim 8, wherein, after modification with said ankyrin repeat domains, the protein is further formulated into a medicament.

10. The method according to claim 7, wherein the protein selected in step b) is further modified with one or more ankyrin repeat domains capable of binding to a mammalian serum albumin.

11. The method according to claim 10, wherein, after modification with one or more ankyrin repeat domains capable of binding to a mammalian serum albumin, the protein is further formulated into a medicament.

12. The method according to claim 4, wherein the ankyrin repeat domain of said selected protein according to the method of claim 1 (A) or said ankyrin repeat domain with the replaced N-terminal capping module according to the method of claim 1 (B) specifically binds to a virus.

* * * * *

UNITED STATES PATENT AND TRADEMARK OFFICE
CERTIFICATE OF CORRECTION

| | | |
|---|---|---|
| PATENT NO. | : 11,242,369 B1 | Page 1 of 1 |
| APPLICATION NO. | : 17/232470 | |
| DATED | : February 8, 2022 | |
| INVENTOR(S) | : Johannes Schilling et al. | |

It is certified that error appears in the above-identified patent and that said Letters Patent is hereby corrected as shown below:

On the Title Page

Item (56), add:
—WO 2021224686 A1 11/2021—

In the Claims

At Column 108 Claim 4, Line 40:
"corresponding to position 15 and a dipeptide GS to N-ter-"

Should be replaced with:
—corresponding to position 15 and a dipeptide GS N-ter—

Signed and Sealed this
Nineteenth Day of April, 2022

Katherine Kelly Vidal
*Director of the United States Patent and Trademark Office*

SEQUENCE LISTING

```
<160> NUMBER OF SEQ ID NOS: 125

<210> SEQ ID NO 1
<211> LENGTH: 30
<212> TYPE: PRT
<213> ORGANISM: Artificial Sequence
<220> FEATURE:
<223> OTHER INFORMATION: Synthetic Construct

<400> SEQUENCE: 1

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic Construct

<400> SEQUENCE: 2

Asp Leu Gly Lys Lys Leu Leu Glu Ala Ala Arg Ala Gly Gln Asp Asp
1               5                   10                  15

Glu Val Arg Ile Leu Leu Lys Ala Gly Ala Asp Val Asn Ala
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic Construct

<400> SEQUENCE: 3

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic Construct
```

```
<400> SEQUENCE: 4

Asp Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

Asp Leu Gly Lys Lys Leu Leu Glu Ala Ala Arg Ala Gly Gln Asp Asp
1               5                   10                  15

Glu Val Arg Ile Leu Ile Ala Asn Gly Ala Pro Phe Thr Thr
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic Construct

<400> SEQUENCE: 6

Asp Leu Gly Lys Lys Leu Leu Glu Ala Ala Arg Ala Gly Gln Asp Asp
1               5                   10                  15

Glu Val Arg Glu Leu Thr Lys Ala Gly Ala Asp Val Asn Ala
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 7

Asp Leu Gly Lys Lys Leu Leu Glu Ala Ala Arg Ala Gly Gln Xaa Asp
1               5                   10                  15

Glu Val Arg Ile Leu Met Ala Asn Gly Ala Asp Val Asn Ala
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 8

Asp Leu Gly Lys Lys Leu Leu Glu Ala Ala Arg Ala Gly Gln Xaa Asp
1               5                   10                  15

Glu Val Arg Glu Leu Leu Lys Ala Gly Ala Asp Val Asn Ala
            20                  25                  30
```

```
<210> SEQ ID NO 9
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 9

Asp Leu Asp Lys Lys Leu Leu Glu Ala Ala Arg Ala Gly Gln Xaa Asp
1               5                   10                  15

Glu Val Arg Glu Leu Thr Lys Ala Gly Ala Asp Val Asn Ala
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 10

Asp Leu Gly Lys Lys Leu Leu Glu Ala Ala Arg Ala Gly Gln Xaa Asp
1               5                   10                  15

Glu Val Arg Glu Leu Ile Lys Ala Gly Ala Asp Val Asn Ala
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 11

Asp Leu Asp Lys Lys Leu Leu Glu Ala Ala Ala Ala Gly Gln Xaa Asp
1               5                   10                  15

Ala Val Arg Glu Leu Leu Lys Ala Gly Ala Asp Val Asn Ala
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 12

Asp Leu Ala Lys Lys Leu Leu Glu Ala Ala Ala Ala Gly Gln Xaa Asp
1               5                   10                  15

Ala Val Arg Glu Leu Val Lys Ala Gly Ala Asp Val Asn Ala
```

```
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 13

Asp Leu Gly Lys Lys Leu Leu Glu Ala Ala Ala Ala Gly Gln Xaa Asp
1               5                   10                  15

Ala Val Arg Glu Leu Ile Lys Ala Gly Ala Asp Val Asn Ala
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 14

Asp Leu Ala Lys Lys Leu Leu Glu Ala Ala Ala Ala Gly Gln Xaa Asp
1               5                   10                  15

Ala Val Arg Glu Leu Ala Lys Ala Gly Ala Asp Val Asn Ala
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 15

Asp Leu Ala Lys Lys Leu Leu Ala Ala Ala Ala Ala Gly Gln Xaa Glu
1               5                   10                  15

Ala Val Glu Gln Leu Leu Lys Ala Gly Ala Asp Val Asn Ala
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa can be any naturally occuring amino acid

<400> SEQUENCE: 16

Asp Leu Gly Lys Lys Leu Leu Ala Ala Ala Ala Ala Gly Gln Xaa Glu
1               5                   10                  15
```

Ala Val Glu Gln Leu Ile Lys Ala Gly Ala Asp Val Asn Ala
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic Construct

<400> SEQUENCE: 17

Asp Leu Gly Lys Lys Leu Leu Glu Ala Ala Arg Ala Gly Gln Ile Asp
1               5                   10                  15
Glu Val Arg Ile Leu Met Ala Asn Gly Ala Asp Val Asn Ala
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic Construct

<400> SEQUENCE: 18

Asp Leu Gly Lys Lys Leu Leu Glu Ala Ala Arg Ala Gly Gln Ile Asp
1               5                   10                  15
Glu Val Arg Glu Leu Leu Lys Ala Gly Ala Asp Val Asn Ala
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic Construct

<400> SEQUENCE: 19

Asp Leu Asp Lys Lys Leu Leu Glu Ala Ala Arg Ala Gly Gln Ile Asp
1               5                   10                  15
Glu Val Arg Glu Leu Thr Lys Ala Gly Ala Asp Val Asn Ala
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic Construct

<400> SEQUENCE: 20

Asp Leu Gly Lys Lys Leu Leu Glu Ala Ala Arg Ala Gly Gln Ile Asp
1               5                   10                  15
Glu Val Arg Glu Leu Ile Lys Ala Gly Ala Asp Val Asn Ala
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic Construct

<400> SEQUENCE: 21

Asp Leu Asp Lys Lys Leu Leu Glu Ala Ala Ala Ala Gly Gln Ile Asp
1               5                   10                  15

Ala Val Arg Glu Leu Leu Lys Ala Gly Ala Asp Val Asn Ala
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic Construct

<400> SEQUENCE: 22

Asp Leu Ala Lys Lys Leu Leu Glu Ala Ala Ala Gly Gln Ile Asp
1               5                   10                  15

Ala Val Arg Glu Leu Val Lys Ala Gly Ala Asp Val Asn Ala
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic Construct

<400> SEQUENCE: 23

Asp Leu Gly Lys Lys Leu Leu Glu Ala Ala Ala Gly Gln Ile Asp
1               5                   10                  15

Ala Val Arg Glu Leu Ile Lys Ala Gly Ala Asp Val Asn Ala
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic Construct

<400> SEQUENCE: 24

Asp Leu Ala Lys Lys Leu Leu Glu Ala Ala Ala Gly Gln Ile Asp
1               5                   10                  15

Ala Val Arg Glu Leu Ala Lys Ala Gly Ala Asp Val Asn Ala
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Asp Leu Ala Lys Lys Leu Leu Ala Ala Ala Ala Gly Gln Ile Glu
1               5                   10                  15

Ala Val Glu Gln Leu Leu Lys Ala Gly Ala Asp Val Asn Ala
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic Construct

<400> SEQUENCE: 26

Asp Leu Gly Lys Lys Leu Leu Ala Ala Ala Ala Gly Gln Ile Glu

```
                 1               5                  10                  15
Ala Val Glu Gln Leu Ile Lys Ala Gly Ala Asp Val Asn Ala
                20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27

Asp Leu Gly Lys Lys Leu Leu Glu Ala Ala Arg Ala Gly Gln Thr Asp
 1               5                  10                  15

Glu Val Arg Ile Leu Met Ala Asn Gly Ala Asp Val Asn Ala
                20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic Construct

<400> SEQUENCE: 28

Asp Leu Gly Lys Lys Leu Leu Glu Ala Ala Arg Ala Gly Gln Thr Asp
 1               5                  10                  15

Glu Val Arg Glu Leu Leu Lys Ala Gly Ala Asp Val Asn Ala
                20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Asp Leu Asp Lys Lys Leu Leu Glu Ala Ala Arg Ala Gly Gln Thr Asp
 1               5                  10                  15

Glu Val Arg Glu Leu Thr Lys Ala Gly Ala Asp Val Asn Ala
                20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic Construct

<400> SEQUENCE: 30

Asp Leu Gly Lys Lys Leu Leu Glu Ala Ala Arg Ala Gly Gln Thr Asp
 1               5                  10                  15

Glu Val Arg Glu Leu Ile Lys Ala Gly Ala Asp Val Asn Ala
                20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic Construct

<400> SEQUENCE: 31
```

```
Asp Leu Asp Lys Lys Leu Leu Glu Ala Ala Ala Ala Gly Gln Thr Asp
1               5                   10                  15

Ala Val Arg Glu Leu Leu Lys Ala Gly Ala Asp Val Asn Ala
            20                  25                  30
```

<210> SEQ ID NO 32
<211> LENGTH: 30
<212> TYPE: PRT
<213> ORGANISM: Artificial Sequence
<220> FEATURE:
<223> OTHER INFORMATION: Synthetic Construct

<400> SEQUENCE: 32

```
Asp Leu Ala Lys Lys Leu Leu Glu Ala Ala Ala Ala Gly Gln Thr Asp
1               5                   10                  15

Ala Val Arg Glu Leu Val Lys Ala Gly Ala Asp Val Asn Ala
            20                  25                  30
```

<210> SEQ ID NO 33
<211> LENGTH: 30
<212> TYPE: PRT
<213> ORGANISM: Artificial Sequence
<220> FEATURE:
<223> OTHER INFORMATION: Synthetic Construct

<400> SEQUENCE: 33

```
Asp Leu Gly Lys Lys Leu Leu Glu Ala Ala Ala Ala Gly Gln Thr Asp
1               5                   10                  15

Ala Val Arg Glu Leu Ile Lys Ala Gly Ala Asp Val Asn Ala
            20                  25                  30
```

<210> SEQ ID NO 34
<211> LENGTH: 30
<212> TYPE: PRT
<213> ORGANISM: Artificial Sequence
<220> FEATURE:
<223> OTHER INFORMATION: Synthetic Construct

<400> SEQUENCE: 34

```
Asp Leu Ala Lys Lys Leu Leu Glu Ala Ala Ala Ala Gly Gln Thr Asp
1               5                   10                  15

Ala Val Arg Glu Leu Ala Lys Ala Gly Ala Asp Val Asn Ala
            20                  25                  30
```

<210> SEQ ID NO 35
<211> LENGTH: 30
<212> TYPE: PRT
<213> ORGANISM: Artificial Sequence
<220> FEATURE:
<223> OTHER INFORMATION: Synthetic Construct

<400> SEQUENCE: 35

```
Asp Leu Ala Lys Lys Leu Leu Ala Ala Ala Ala Ala Gly Gln Thr Glu
1               5                   10                  15

Ala Val Glu Gln Leu Leu Lys Ala Gly Ala Asp Val Asn Ala
            20                  25                  30
```

<210> SEQ ID NO 36
<211> LENGTH: 30
<212> TYPE: PRT
<213> ORGANISM: Artificial Sequence
<220> FEATURE:
<223> OTHER INFORMATION: Synthetic Construct

<400> SEQUENCE: 36

```
Asp Leu Gly Lys Lys Leu Leu Ala Ala Ala Ala Gly Gln Thr Glu
1               5                   10                  15

Ala Val Glu Gln Leu Ile Lys Ala Gly Ala Asp Val Asn Ala
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic Construct

<400> SEQUENCE: 37

Asp Leu Gly Lys Lys Leu Leu Glu Ala Ala Arg Ala Gly Gln Ala Asp
1               5                   10                  15

Glu Val Arg Ile Leu Met Ala Asn Gly Ala Asp Val Asn Ala
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic Construct

<400> SEQUENCE: 38

Asp Leu Gly Lys Lys Leu Leu Glu Ala Ala Arg Ala Gly Gln Ala Asp
1               5                   10                  15

Glu Val Arg Glu Leu Leu Lys Ala Gly Ala Asp Val Asn Ala
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic Construct

<400> SEQUENCE: 39

Asp Leu Asp Lys Lys Leu Leu Glu Ala Ala Arg Ala Gly Gln Ala Asp
1               5                   10                  15

Glu Val Arg Glu Leu Thr Lys Ala Gly Ala Asp Val Asn Ala
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic Construct

<400> SEQUENCE: 40

Asp Leu Gly Lys Lys Leu Leu Glu Ala Ala Arg Ala Gly Gln Ala Asp
1               5                   10                  15

Glu Val Arg Glu Leu Ile Lys Ala Gly Ala Asp Val Asn Ala
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic Construct
```

```
<400> SEQUENCE: 41

Asp Leu Asp Lys Lys Leu Leu Glu Ala Ala Ala Ala Gly Gln Ala Asp
1               5                   10                  15

Ala Val Arg Glu Leu Leu Lys Ala Gly Ala Asp Val Asn Ala
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic Construct

<400> SEQUENCE: 42

Asp Leu Ala Lys Lys Leu Leu Glu Ala Ala Ala Ala Gly Gln Ala Asp
1               5                   10                  15

Ala Val Arg Glu Leu Val Lys Ala Gly Ala Asp Val Asn Ala
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Synthetic Construct

<400> SEQUENCE: 43

Asp Leu Gly Lys Lys Leu Leu Glu Ala Ala Ala Ala Gly Gln Ala Asp
1               5                   10                  15

Ala Val Arg Glu Leu Ile Lys Ala Gly Ala Asp Val Asn Ala
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Synthetic Construct

<400> SEQUENCE: 44

Asp Leu Ala Lys Lys Leu Leu Glu Ala Ala Ala Ala Gly Gln Ala Asp
1               5                   10                  15

Ala Val Arg Glu Leu Ala Lys Ala Gly Ala Asp Val Asn Ala
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic Construct

<400> SEQUENCE: 45

Asp Leu Ala Lys Lys Leu Leu Ala Ala Ala Ala Gly Gln Ala Glu
1               5                   10                  15

Ala Val Glu Gln Leu Leu Lys Ala Gly Ala Asp Val Asn Ala
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Synthetic Construct
```

```
<400> SEQUENCE: 46

Asp Leu Gly Lys Lys Leu Leu Ala Ala Ala Ala Gly Gln Ala Glu
1               5                   10                  15

Ala Val Glu Gln Leu Ile Lys Ala Gly Ala Asp Val Asn Ala
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Synthetic Construct

<400> SEQUENCE: 47

Asp Leu Gly Lys Lys Leu Leu Glu Ala Ala Arg Ala Gly Gln Val Asp
1               5                   10                  15

Glu Val Arg Ile Leu Met Ala Asn Gly Ala Asp Val Asn Ala
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic Construct

<400> SEQUENCE: 48

Asp Leu Gly Lys Lys Leu Leu Glu Ala Ala Arg Ala Gly Gln Val Asp
1               5                   10                  15

Glu Val Arg Glu Leu Leu Lys Ala Gly Ala Asp Val Asn Ala
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic Construct

<400> SEQUENCE: 49

Asp Leu Asp Lys Lys Leu Leu Glu Ala Ala Arg Ala Gly Gln Val Asp
1               5                   10                  15

Glu Val Arg Glu Leu Thr Lys Ala Gly Ala Asp Val Asn Ala
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic Construct

<400> SEQUENCE: 50

Asp Leu Gly Lys Lys Leu Leu Glu Ala Ala Arg Ala Gly Gln Val Asp
1               5                   10                  15

Glu Val Arg Glu Leu Ile Lys Ala Gly Ala Asp Val Asn Ala
            20                  25                  30

<210> SEQ ID NO 51
<211> LENGTH: 30
<212> TYPE: PRT
<213> ORGANISM: Artificial Sequence
<220> FEATURE:
```

<223> OTHER INFORMATION: Synthetic Construct

<400> SEQUENCE: 51

Asp Leu Asp Lys Lys Leu Leu Glu Ala Ala Ala Ala Gly Gln Val Asp
1               5                   10                  15

Ala Val Arg Glu Leu Leu Lys Ala Gly Ala Asp Val Asn Ala
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct

<400> SEQUENCE: 52

Asp Leu Ala Lys Lys Leu Leu Glu Ala Ala Ala Ala Gly Gln Val Asp
1               5                   10                  15

Ala Val Arg Glu Leu Val Lys Ala Gly Ala Asp Val Asn Ala
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic Construct

<400> SEQUENCE: 53

Asp Leu Gly Lys Lys Leu Leu Glu Ala Ala Ala Ala Gly Gln Val Asp
1               5                   10                  15

Ala Val Arg Glu Leu Ile Lys Ala Gly Ala Asp Val Asn Ala
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic Construct

<400> SEQUENCE: 54

Asp Leu Ala Lys Lys Leu Leu Glu Ala Ala Ala Ala Gly Gln Val Asp
1               5                   10                  15

Ala Val Arg Glu Leu Ala Lys Ala Gly Ala Asp Val Asn Ala
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Synthetic Construct

<400> SEQUENCE: 55

Asp Leu Ala Lys Lys Leu Leu Ala Ala Ala Ala Gly Gln Val Glu
1               5                   10                  15

Ala Val Glu Gln Leu Leu Lys Ala Gly Ala Asp Val Asn Ala
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Synthetic Construct

<400> SEQUENCE: 56

Asp Leu Gly Lys Lys Leu Leu Ala Ala Ala Ala Gly Gln Val Glu
1               5                   10                  15

Ala Val Glu Gln Leu Ile Lys Ala Gly Ala Asp Val Asn Ala
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Synthetic Construct

<400> SEQUENCE: 57

Asp Leu Gly Lys Lys Leu Leu Glu Ala Ala Arg Ala Gly Gln Leu Asp
1               5                   10                  15

Glu Val Arg Ile Leu Met Ala Asn Gly Ala Asp Val Asn Ala
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Synthetic Construct

<400> SEQUENCE: 58

Asp Leu Gly Lys Lys Leu Leu Glu Ala Ala Arg Ala Gly Gln Leu Asp
1               5                   10                  15

Glu Val Arg Glu Leu Leu Lys Ala Gly Ala Asp Val Asn Ala
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Synthetic Construct

<400> SEQUENCE: 59

Asp Leu Asp Lys Lys Leu Leu Glu Ala Ala Arg Ala Gly Gln Leu Asp
1               5                   10                  15

Glu Val Arg Glu Leu Thr Lys Ala Gly Ala Asp Val Asn Ala
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Synthetic Construct

<400> SEQUENCE: 60

Asp Leu Gly Lys Lys Leu Leu Glu Ala Ala Arg Ala Gly Gln Leu Asp
1               5                   10                  15

Glu Val Arg Glu Leu Ile Lys Ala Gly Ala Asp Val Asn Ala
            20                  25                  30

<210> SEQ ID NO 61
<211> LENGTH: 30
<212> TYPE: PRT

```
<213> ORGANISM: Artificial Sequence
<220> FEATURE:
<223> OTHER INFORMATION: Synthetic Construct

<400> SEQUENCE: 61

Asp Leu Asp Lys Lys Leu Leu Glu Ala Ala Ala Ala Gly Gln Leu Asp
1               5                   10                  15

Ala Val Arg Glu Leu Leu Lys Ala Gly Ala Asp Val Asn Ala
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Synthetic Construct

<400> SEQUENCE: 62

Asp Leu Ala Lys Lys Leu Leu Glu Ala Ala Ala Ala Gly Gln Leu Asp
1               5                   10                  15

Ala Val Arg Glu Leu Val Lys Ala Gly Ala Asp Val Asn Ala
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Synthetic Construct

<400> SEQUENCE: 63

Asp Leu Gly Lys Lys Leu Leu Glu Ala Ala Ala Ala Gly Gln Leu Asp
1               5                   10                  15

Ala Val Arg Glu Leu Ile Lys Ala Gly Ala Asp Val Asn Ala
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Synthetic Construct

<400> SEQUENCE: 64

Asp Leu Ala Lys Lys Leu Leu Glu Ala Ala Ala Ala Gly Gln Leu Asp
1               5                   10                  15

Ala Val Arg Glu Leu Ala Lys Ala Gly Ala Asp Val Asn Ala
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Synthetic Construct

<400> SEQUENCE: 65

Asp Leu Ala Lys Lys Leu Leu Ala Ala Ala Ala Ala Gly Gln Leu Glu
1               5                   10                  15

Ala Val Glu Gln Leu Leu Lys Ala Gly Ala Asp Val Asn Ala
            20                  25                  30

<210> SEQ ID NO 66
<211> LENGTH: 30
```

```
<212> TYPE: PRT
<213> ORGANISM: Artificial Sequence
<220> FEATURE:
<223> OTHER INFORMATION: Synthetic Construct

<400> SEQUENCE: 66

Asp Leu Gly Lys Lys Leu Leu Ala Ala Ala Ala Gly Gln Leu Glu
1               5                   10                  15

Ala Val Glu Gln Leu Ile Lys Ala Gly Ala Asp Val Asn Ala
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Synthetic Construct

<400> SEQUENCE: 67

Asp Leu Gly Lys Lys Leu Leu Glu Ala Ala Arg Ala Gly Gln Met Asp
1               5                   10                  15

Glu Val Arg Ile Leu Met Ala Asn Gly Ala Asp Val Asn Ala
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Synthetic Construct

<400> SEQUENCE: 68

Asp Leu Gly Lys Lys Leu Leu Glu Ala Ala Arg Ala Gly Gln Met Asp
1               5                   10                  15

Glu Val Arg Glu Leu Leu Lys Ala Gly Ala Asp Val Asn Ala
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Synthetic Construct

<400> SEQUENCE: 69

Asp Leu Asp Lys Lys Leu Leu Glu Ala Ala Arg Ala Gly Gln Met Asp
1               5                   10                  15

Glu Val Arg Glu Leu Thr Lys Ala Gly Ala Asp Val Asn Ala
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Synthetic Construct

<400> SEQUENCE: 70

Asp Leu Gly Lys Lys Leu Leu Glu Ala Ala Arg Ala Gly Gln Met Asp
1               5                   10                  15

Glu Val Arg Glu Leu Ile Lys Ala Gly Ala Asp Val Asn Ala
            20                  25                  30

<210> SEQ ID NO 71
```

```
<211> LENGTH: 30
<212> TYPE: PRT
<213> ORGANISM: Artificial Sequence
<220> FEATURE:
<223> OTHER INFORMATION: Synthetic Construct

<400> SEQUENCE: 71

Asp Leu Asp Lys Lys Leu Leu Glu Ala Ala Ala Ala Gly Gln Met Asp
1               5                   10                  15

Ala Val Arg Glu Leu Leu Lys Ala Gly Ala Asp Val Asn Ala
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Synthetic Construct

<400> SEQUENCE: 72

Asp Leu Ala Lys Lys Leu Leu Glu Ala Ala Ala Ala Gly Gln Met Asp
1               5                   10                  15

Ala Val Arg Glu Leu Val Lys Ala Gly Ala Asp Val Asn Ala
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Synthetic Construct

<400> SEQUENCE: 73

Asp Leu Gly Lys Lys Leu Leu Glu Ala Ala Ala Ala Gly Gln Met Asp
1               5                   10                  15

Ala Val Arg Glu Leu Ile Lys Ala Gly Ala Asp Val Asn Ala
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Synthetic Construct

<400> SEQUENCE: 74

Asp Leu Ala Lys Lys Leu Leu Glu Ala Ala Ala Ala Gly Gln Met Asp
1               5                   10                  15

Ala Val Arg Glu Leu Ala Lys Ala Gly Ala Asp Val Asn Ala
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Synthetic Construct

<400> SEQUENCE: 75

Asp Leu Ala Lys Lys Leu Leu Ala Ala Ala Ala Ala Gly Gln Met Glu
1               5                   10                  15

Ala Val Glu Gln Leu Leu Lys Ala Gly Ala Asp Val Asn Ala
            20                  25                  30
```

-continued

```
<210> SEQ ID NO 76
<211> LENGTH: 30
<212> TYPE: PRT
<213> ORGANISM: Artificial Sequence
<220> FEATURE:
<223> OTHER INFORMATION: Synthetic Construct

<400> SEQUENCE: 76

Asp Leu Gly Lys Lys Leu Leu Ala Ala Ala Ala Ala Gly Gln Met Glu
1               5                   10                  15

Ala Val Glu Gln Leu Ile Lys Ala Gly Ala Asp Val Asn Ala
            20                  25                  30

<210> SEQ ID NO 77
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 13
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 18
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid
<220> FEATURE:
<221> NAME/KEY: VARIANT
<222> LOCATION: 27
<223> OTHER INFORMATION: Xaa can be any naturally occuring amino acid

<400> SEQUENCE: 77

Xaa Asp Xaa Xaa Gly Xaa Thr Pro Leu His Leu Ala Xaa Xaa Xaa Gly
1               5                   10                  15
```

```
Xaa Xaa Xaa Val Val Xaa Leu Leu Leu Xaa Xaa Gly Ala Asp Val Asn
            20                  25                  30

Ala

<210> SEQ ID NO 78
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 27
<223> OTHER INFORMATION: Xaa can be any naturally occuring amino acid

<400> SEQUENCE: 78

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 79
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
```

-continued

```
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 27
<223> OTHER INFORMATION: Xaa can be any naturally occuring amino acid

<400> SEQUENCE: 79

Ser Xaa Xaa Xaa Gly Xaa Thr Pro Leu His Xaa Ala Ala Xaa Xaa Gly
1               5                   10                  15

His Leu Glu Ile Val Asp Val Leu Leu Ala Xaa Gly Ala Asp Val Asn
            20                  25                  30

Ala

<210> SEQ ID NO 80
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid

<400> SEQUENCE: 80

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Asn Gly Ala Asp Val Asn
            20                  25                  30

Ala

<210> SEQ ID NO 81
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
```

```
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid

<400> SEQUENCE: 81

Lys Asp Xaa Xaa Gly Xaa Thr Pro Leu His Leu Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 82
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 27
<223> OTHER INFORMATION: Xaa can be any naturally occuring amino acid

<400> SEQUENCE: 82

Xaa Asp Xaa Xaa Gly Xaa Thr Pro Leu His Xaa Ala Ala Xaa Xaa Gly
1               5                   10                  15

His Leu Glu Val Val Lys Leu Leu Leu Glu Xaa Gly Ala Asp Val Asn
            20                  25                  30

Ala

<210> SEQ ID NO 83
<211> LENGTH: 28
<212> TYPE: PRT
<213> ORGANISM: Artificial Sequence
```

```
<220> FEATURE:
<223> OTHER INFORMATION: Synthetic Construct

<400> SEQUENCE: 83

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Leu Asn
            20                  25

<210> SEQ ID NO 84
<211> LENGTH: 28
<212> TYPE: PRT
<213> ORGANISM: Artificial Sequence
<220> FEATURE:
<223> OTHER INFORMATION: Synthetic Construct

<400> SEQUENCE: 84

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Ala Ala
            20                  25

<210> SEQ ID NO 85
<211> LENGTH: 28
<212> TYPE: PRT
<213> ORGANISM: Artificial Sequence
<220> FEATURE:
<223> OTHER INFORMATION: Synthetic Construct

<400> SEQUENCE: 85

Gln Asp Lys Phe Gly Lys Thr Pro Phe Asp Leu Ala Ile Asp Asn Gly
1               5                   10                  15

Asn Glu Asp Ile Ala Glu Val Leu Gln Lys Ala Ala
            20                  25

<210> SEQ ID NO 86
<211> LENGTH: 28
<212> TYPE: PRT
<213> ORGANISM: Artificial Sequence
<220> FEATURE:
<223> OTHER INFORMATION: Synthetic Construct

<400> SEQUENCE: 86

Gln Asp Lys Phe Gly Lys Thr Pro Phe Asp Leu Ala Ile Arg Glu Gly
1               5                   10                  15

His Glu Asp Ile Ala Glu Val Leu Gln Lys Ala Ala
            20                  25

<210> SEQ ID NO 87
<211> LENGTH: 28
<212> TYPE: PRT
<213> ORGANISM: Artificial Sequence
<220> FEATURE:
<223> OTHER INFORMATION: Synthetic Construct

<400> SEQUENCE: 87

Gln Asp Lys Ser Gly Lys Thr Pro Ala Asp Leu Ala Ala Asp Ala Gly
1               5                   10                  15

His Glu Asp Ile Ala Glu Val Leu Gln Lys Ala Ala
            20                  25

<210> SEQ ID NO 88
<211> LENGTH: 28
<212> TYPE: PRT
```

```
<213> ORGANISM: Artificial Sequence
<220> FEATURE:
<223> OTHER INFORMATION: Synthetic Construct

<400> SEQUENCE: 88

Gln Asp Ser Ala Gly Lys Thr Pro Ala Asp Leu Ala Ala Asp Ala Gly
1               5                   10                  15

His Glu Glu Ile Ala Glu Val Leu Gln Lys Ala Ala
            20                  25

<210> SEQ ID NO 89
<211> LENGTH: 28
<212> TYPE: PRT
<213> ORGANISM: Artificial Sequence
<220> FEATURE:
<223> OTHER INFORMATION: Synthetic Construct

<400> SEQUENCE: 89

Gln Asp Lys Ala Gly Leu Thr Pro Ala Asp Leu Ala Ala Asp Ala Gly
1               5                   10                  15

His Glu Glu Ile Ala Glu Val Leu Gln Lys Ala Ala
            20                  25

<210> SEQ ID NO 90
<211> LENGTH: 28
<212> TYPE: PRT
<213> ORGANISM: Artificial Sequence
<220> FEATURE:
<223> OTHER INFORMATION: Synthetic Construct

<400> SEQUENCE: 90

Gln Asp Ser Leu Gly Lys Thr Pro Ala Asp Leu Ala Ala Leu Ala Gly
1               5                   10                  15

His Glu Glu Ile Ala Glu Val Leu Gln Lys Ala Ala
            20                  25

<210> SEQ ID NO 91
<211> LENGTH: 28
<212> TYPE: PRT
<213> ORGANISM: Artificial Sequence
<220> FEATURE:
<223> OTHER INFORMATION: Synthetic Construct

<400> SEQUENCE: 91

Gln Asp Lys Ala Gly Gln Thr Pro Ala Asp Leu Ala Ala Asp Ala Gly
1               5                   10                  15

His Glu Glu Ile Ala Glu Val Leu Gln Lys Ala Ala
            20                  25

<210> SEQ ID NO 92
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
```

```
<220> FEATURE:
<221> NAME/KEY: VARIANT
<222> LOCATION: 14
<223> OTHER INFORMATION: Xaa can be any naturally occuring amino acid

<400> SEQUENCE: 92

Gln Asp Xaa Xaa Gly Xaa Thr Pro Ala Asp Leu Ala Ala Xaa Ala Gly
1               5                   10                  15

His Glu Glu Ile Ala Glu Val Leu Gln Lys Ala Ala
            20                  25

<210> SEQ ID NO 93
<211> LENGTH: 103
<212> TYPE: PRT
<213> ORGANISM: Artificial Sequence
<220> FEATURE:
<223> OTHER INFORMATION: Synthetic Construct

<400> SEQUENCE: 93

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 94
<211> LENGTH: 103
<212> TYPE: PRT
<213> ORGANISM: Artificial Sequence
<220> FEATURE:
<223> OTHER INFORMATION: Synthetic Construct

<400> SEQUENCE: 94

Met Arg Gly Ser His His His His His His Gly Ser Asp Leu Gly Lys
1               5                   10                  15

Lys Leu Leu Glu Ala Ala Arg Ala Gly Gln Leu Asp Glu Val Arg Ile
            20                  25                  30

Leu Met Ala Asn Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 95
<211> LENGTH: 103
<212> TYPE: PRT
```

```
<213> ORGANISM: Artificial Sequence
<220> FEATURE:
<223> OTHER INFORMATION: Synthetic Construct

<400> SEQUENCE: 95

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 96
<211> LENGTH: 103
<212> TYPE: PRT
<213> ORGANISM: Artificial Sequence
<220> FEATURE:
<223> OTHER INFORMATION: Synthetic Construct

<400> SEQUENCE: 96

Met Arg Gly Ser His His His His His His Gly Ser Asp Leu Gly Lys
1               5                   10                  15

Lys Leu Leu Glu Ala Ala Arg Ala Gly Gln Leu Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 97
<211> LENGTH: 103
<212> TYPE: PRT
<213> ORGANISM: Artificial Sequence
<220> FEATURE:
<223> OTHER INFORMATION: Synthetic Construct

<400> SEQUENCE: 97

Met Arg Gly Ser His His His His His His Gly Ser Asp Leu Gly Lys
1               5                   10                  15

Lys Leu Leu Glu Ala Ala Arg Ala Gly Gln Met Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60
```

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 98
<211> LENGTH: 103
<212> TYPE: PRT
<213> ORGANISM: Artificial Sequence
<220> FEATURE:
<223> OTHER INFORMATION: Synthetic Construct

<400> SEQUENCE: 98

Met Arg Gly Ser His His His His His His Gly Ser Asp Leu Gly Lys
1               5                   10                  15

Lys Leu Leu Glu Ala Ala Arg Ala Gly Gln Ile Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 99
<211> LENGTH: 103
<212> TYPE: PRT
<213> ORGANISM: Artificial Sequence
<220> FEATURE:
<223> OTHER INFORMATION: Synthetic Construct

<400> SEQUENCE: 99

Met Arg Gly Ser His His His His His His Gly Ser Asp Leu Gly Lys
1               5                   10                  15

Lys Leu Leu Glu Ala Ala Arg Ala Gly Gln Thr Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 100
<211> LENGTH: 103
<212> TYPE: PRT
<213> ORGANISM: Artificial Sequence
<220> FEATURE:
<223> OTHER INFORMATION: Synthetic Construct

<400> SEQUENCE: 100

```
Met Arg Gly Ser His His His His His Gly Ser Asp Leu Gly Lys
1               5                   10                  15

Lys Leu Leu Glu Ala Ala Arg Ala Gly Gln Ala Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100
```

<210> SEQ ID NO 101
<211> LENGTH: 103
<212> TYPE: PRT
<213> ORGANISM: Artificial Sequence
<220> FEATURE:
<223> OTHER INFORMATION: Synthetic Construct

<400> SEQUENCE: 101

```
Met Arg Gly Ser His His His His His Gly Ser Asp Leu Gly Lys
1               5                   10                  15

Lys Leu Leu Glu Ala Ala Arg Ala Gly Gln Val Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100
```

<210> SEQ ID NO 102
<211> LENGTH: 103
<212> TYPE: PRT
<213> ORGANISM: Artificial Sequence
<220> FEATURE:
<223> OTHER INFORMATION: Synthetic Construct

<400> SEQUENCE: 102

```
Met Arg Gly Ser His His His His His Gly Ser Asp Leu Gly Lys
1               5                   10                  15

Lys Leu Leu Glu Ala Ala Arg Ala Gly Gln Ser Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80
```

Lys Thr Ala Phe Asp Ile Ser Ile Asp Asn Gly Asn Glu Asp Leu Ala
            85                  90                  95

Glu Ile Leu Gln Lys Leu Asn
            100

<210> SEQ ID NO 103
<211> LENGTH: 103
<212> TYPE: PRT
<213> ORGANISM: Artificial Sequence
<220> FEATURE:
<223> OTHER INFORMATION: Synthetic Construct

<400> SEQUENCE: 103

Met Arg Gly Ser His His His His His Gly Ser Asp Leu Gly Lys
1               5                   10                  15

Lys Leu Leu Glu Ala Ala Arg Ala Gly Gln Asn Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
            85                  90                  95

Glu Ile Leu Gln Lys Leu Asn
            100

<210> SEQ ID NO 104
<211> LENGTH: 103
<212> TYPE: PRT
<213> ORGANISM: Artificial Sequence
<220> FEATURE:
<223> OTHER INFORMATION: Synthetic Construct

<400> SEQUENCE: 104

Met Arg Gly Ser His His His His His His Gly Ser Asp Leu Gly Lys
1               5                   10                  15

Lys Leu Leu Glu Ala Ala Arg Ala Gly Gln Gln Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
            85                  90                  95

Glu Ile Leu Gln Lys Leu Asn
            100

<210> SEQ ID NO 105
<211> LENGTH: 103
<212> TYPE: PRT
<213> ORGANISM: Artificial Sequence
<220> FEATURE:
<223> OTHER INFORMATION: Synthetic Construct

<400> SEQUENCE: 105

Met Arg Gly Ser His His His His His Gly Ser Asp Leu Gly Lys
1               5                   10                  15

Lys Leu Leu Glu Ala Ala Arg Ala Gly Gln Lys Asp Glu Val Arg Glu
            20                  25                  30

Leu Leu Lys Ala Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 106
<211> LENGTH: 103
<212> TYPE: PRT
<213> ORGANISM: Artificial Sequence
<220> FEATURE:
<223> OTHER INFORMATION: Synthetic Construct

<400> SEQUENCE: 106

Met Arg Gly Ser His His His His His Gly Ser Asp Leu Gly Lys
1               5                   10                  15

Lys Leu Leu Glu Ala Ala Arg Ala Gly Gln Arg Asp Glu Val Arg Glu
            20                  25                  30

Leu Leu Lys Ala Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 107
<211> LENGTH: 103
<212> TYPE: PRT
<213> ORGANISM: Artificial Sequence
<220> FEATURE:
<223> OTHER INFORMATION: Synthetic Construct

<400> SEQUENCE: 107

Met Arg Gly Ser His His His His His Gly Ser Asp Leu Gly Lys
1               5                   10                  15

Lys Leu Leu Glu Ala Ala Arg Ala Gly Gln Glu Asp Glu Val Arg Glu
            20                  25                  30

Leu Leu Lys Ala Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 108
<211> LENGTH: 103
<212> TYPE: PRT
<213> ORGANISM: Artificial Sequence
<220> FEATURE:
<223> OTHER INFORMATION: Synthetic Construct

<400> SEQUENCE: 108

Met Arg Gly Ser His His His His His His Asp Ala Asp Leu Ala Lys
1               5                   10                  15

Lys Leu Leu Ala Ala Ala Ala Ala Gly Gln Asp Glu Ala Val Glu Gln
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 109
<211> LENGTH: 103
<212> TYPE: PRT
<213> ORGANISM: Artificial Sequence
<220> FEATURE:
<223> OTHER INFORMATION: Synthetic Construct

<400> SEQUENCE: 109

Met Arg Gly Ser His His His His His His Asp Ala Asp Leu Ala Lys
1               5                   10                  15

Lys Leu Leu Ala Ala Ala Ala Ala Gly Gln Leu Glu Ala Val Glu Gln
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 110
<211> LENGTH: 30
<212> TYPE: PRT
<213> ORGANISM: Artificial Sequence
<220> FEATURE:
<223> OTHER INFORMATION: Synthetic Construct

<400> SEQUENCE: 110

Asp Leu Gly Lys Lys Leu Leu Gln Ala Ala Arg Ala Gly Gln Leu Asp
1               5                   10                  15

```
Glu Val Arg Glu Leu Leu Lys Ala Gly Ala Asp Val Asn Ala
         20                  25                  30
```

<210> SEQ ID NO 111
<211> LENGTH: 28
<212> TYPE: PRT
<213> ORGANISM: Artificial Sequence
<220> FEATURE:
<223> OTHER INFORMATION: Synthetic construct

<400> SEQUENCE: 111

```
Gln Asp Lys Ser Gly Lys Thr Pro Ala Asp Leu Ala Ala Arg Ala Gly
 1               5                  10                  15

His Gln Asp Ile Ala Glu Val Leu Gln Lys Ala Ala
         20                  25
```

<210> SEQ ID NO 112
<211> LENGTH: 28
<212> TYPE: PRT
<213> ORGANISM: Artificial Sequence
<220> FEATURE:
<223> OTHER INFORMATION: Synthetic Construct

<400> SEQUENCE: 112

```
Gln Asp Lys Phe Gly Lys Thr Ala Glu Asp Leu Ala Lys Asp Asn Gly
 1               5                  10                  15

Asn Gln Asp Ile Ala Asp Leu Leu Glu Lys Ala Leu
         20                  25
```

<210> SEQ ID NO 113
<211> LENGTH: 136
<212> TYPE: PRT
<213> ORGANISM: Artificial Sequence
<220> FEATURE:
<223> OTHER INFORMATION: Synthetic Construct

<400> SEQUENCE: 113

```
Met Arg Gly Ser His His His His His His Gly Ser Asp Leu Gly Lys
 1               5                  10                  15

Lys Leu Leu Glu Ala Ala Arg Ala Gly Gln Asp Asp Glu Val Arg Glu
         20                  25                  30

Leu Leu Lys Ala Gly Ala Asp Val Asn Ala Lys Asp Tyr Phe Ser His
         35                  40                  45

Thr Pro Leu His Leu Ala Ala Arg Asn Gly His Leu Lys Ile Val Glu
         50                  55                  60

Val Leu Leu Lys Ala Gly Ala Asp Val Asn Ala Lys Asp Phe Ala Gly
65                  70                  75                  80

Lys Thr Pro Leu His Leu Ala Ala Asn Glu Gly His Leu Glu Ile Val
                 85                  90                  95

Glu Val Leu Leu Lys Ala Gly Ala Asp Val Asn Ala Gln Asp Ile Phe
                100                 105                 110

Gly Lys Thr Pro Ala Asp Ile Ala Ala Asp Ala Gly His Glu Asp Ile
            115                 120                 125

Ala Glu Val Leu Gln Lys Ala Ala
        130                 135
```

<210> SEQ ID NO 114
<211> LENGTH: 136
<212> TYPE: PRT
<213> ORGANISM: Artificial Sequence
<220> FEATURE:
<223> OTHER INFORMATION: Synthetic Construct

<400> SEQUENCE: 114

Met Arg Gly Ser His His His His His Gly Ser Asp Leu Gly Lys
1               5                   10                  15

Lys Leu Leu Glu Ala Ala Arg Ala Gly Gln Leu Asp Glu Val Arg Glu
            20                  25                  30

Leu Leu Lys Ala Gly Ala Asp Val Asn Ala Lys Asp Tyr Phe Ser His
        35                  40                  45

Thr Pro Leu His Leu Ala Ala Arg Asn Gly His Leu Lys Ile Val Glu
    50                  55                  60

Val Leu Leu Lys Ala Gly Ala Asp Val Asn Ala Lys Asp Phe Ala Gly
65                  70                  75                  80

Lys Thr Pro Leu His Leu Ala Ala Asn Glu Gly His Leu Glu Ile Val
                85                  90                  95

Glu Val Leu Leu Lys Ala Gly Ala Asp Val Asn Ala Gln Asp Ile Phe
            100                 105                 110

Gly Lys Thr Pro Ala Asp Ile Ala Ala Asp Ala Gly His Glu Asp Ile
        115                 120                 125

Ala Glu Val Leu Gln Lys Ala Ala
    130                 135

<210> SEQ ID NO 115
<211> LENGTH: 136
<212> TYPE: PRT
<213> ORGANISM: Artificial Sequence
<220> FEATURE:
<223> OTHER INFORMATION: Synthetic Construct

<400> SEQUENCE: 115

Met Arg Gly Ser His His His His His Gly Ser Asp Leu Gly Lys
1               5                   10                  15

Lys Leu Leu Glu Ala Ala Arg Ala Gly Gln Val Asp Glu Val Arg Glu
            20                  25                  30

Leu Leu Lys Ala Gly Ala Asp Val Asn Ala Lys Asp Tyr Phe Ser His
        35                  40                  45

Thr Pro Leu His Leu Ala Ala Arg Asn Gly His Leu Lys Ile Val Glu
    50                  55                  60

Val Leu Leu Lys Ala Gly Ala Asp Val Asn Ala Lys Asp Phe Ala Gly
65                  70                  75                  80

Lys Thr Pro Leu His Leu Ala Ala Asn Glu Gly His Leu Glu Ile Val
                85                  90                  95

Glu Val Leu Leu Lys Ala Gly Ala Asp Val Asn Ala Gln Asp Ile Phe
            100                 105                 110

Gly Lys Thr Pro Ala Asp Ile Ala Ala Asp Ala Gly His Glu Asp Ile
        115                 120                 125

Ala Glu Val Leu Gln Lys Ala Ala
    130                 135

<210> SEQ ID NO 116
<211> LENGTH: 136
<212> TYPE: PRT
<213> ORGANISM: Artificial Sequence
<220> FEATURE:
<223> OTHER INFORMATION: Synthetic Construct

<400> SEQUENCE: 116

Met Arg Gly Ser His His His His His Gly Ser Asp Leu Asp Lys
1               5                   10                  15

```
Lys Leu Leu Glu Ala Ala Arg Ala Gly Gln Asp Asp Glu Val Arg Ile
            20                  25                  30

Leu Met Ala Asn Gly Ala Asp Val Asn Ala Arg Asp Ser Thr Gly Trp
        35                  40                  45

Thr Pro Leu His Leu Ala Ala Pro Trp Gly His Pro Glu Ile Val Glu
    50                  55                  60

Val Leu Leu Lys Asn Gly Ala Asp Val Asn Ala Ala Asp Phe Gln Gly
65                  70                  75                  80

Trp Thr Pro Leu His Leu Ala Ala Val Gly His Leu Glu Ile Val
                85                  90                  95

Glu Val Leu Leu Lys Tyr Gly Ala Asp Val Asn Ala Gln Asp Lys Phe
                100                 105                 110

Gly Lys Thr Ala Phe Asp Ile Ser Ile Asp Asn Gly Asn Glu Asp Leu
            115                 120                 125

Ala Glu Ile Leu Gln Lys Ala Ala
    130                 135

<210> SEQ ID NO 117
<211> LENGTH: 136
<212> TYPE: PRT
<213> ORGANISM: Artificial Sequence
<220> FEATURE:
<223> OTHER INFORMATION: Synthetic Construct

<400> SEQUENCE: 117

Met Arg Gly Ser His His His His His Gly Ser Asp Leu Asp Lys
1               5                   10                  15

Lys Leu Leu Glu Ala Ala Arg Ala Gly Gln Leu Asp Glu Val Arg Ile
            20                  25                  30

Leu Met Ala Asn Gly Ala Asp Val Asn Ala Arg Asp Ser Thr Gly Trp
        35                  40                  45

Thr Pro Leu His Leu Ala Ala Pro Trp Gly His Pro Glu Ile Val Glu
    50                  55                  60

Val Leu Leu Lys Asn Gly Ala Asp Val Asn Ala Ala Asp Phe Gln Gly
65                  70                  75                  80

Trp Thr Pro Leu His Leu Ala Ala Val Gly His Leu Glu Ile Val
                85                  90                  95

Glu Val Leu Leu Lys Tyr Gly Ala Asp Val Asn Ala Gln Asp Lys Phe
                100                 105                 110

Gly Lys Thr Ala Phe Asp Ile Ser Ile Asp Asn Gly Asn Glu Asp Leu
            115                 120                 125

Ala Glu Ile Leu Gln Lys Ala Ala
    130                 135

<210> SEQ ID NO 118
<211> LENGTH: 136
<212> TYPE: PRT
<213> ORGANISM: Artificial Sequence
<220> FEATURE:
<223> OTHER INFORMATION: Synthetic Construct

<400> SEQUENCE: 118

Met Arg Gly Ser His His His His His Gly Ser Asp Leu Asp Lys
1               5                   10                  15

Lys Leu Leu Glu Ala Ala Arg Ala Gly Gln Val Asp Glu Val Arg Ile
            20                  25                  30

Leu Met Ala Asn Gly Ala Asp Val Asn Ala Arg Asp Ser Thr Gly Trp
```

```
                    35                  40                  45
Thr Pro Leu His Leu Ala Ala Pro Trp Gly His Pro Glu Ile Val Glu
    50                  55                  60

Val Leu Leu Lys Asn Gly Ala Asp Val Asn Ala Ala Asp Phe Gln Gly
65                  70                  75                  80

Trp Thr Pro Leu His Leu Ala Ala Val Gly His Leu Glu Ile Val
                85                  90                  95

Glu Val Leu Leu Lys Tyr Gly Asp Val Asn Ala Gln Asp Lys Phe
                100                 105                 110

Gly Lys Thr Ala Phe Asp Ile Ser Ile Asp Asn Gly Asn Glu Asp Leu
                115                 120                 125

Ala Glu Ile Leu Gln Lys Ala Ala
    130                 135

<210> SEQ ID NO 119
<211> LENGTH: 136
<212> TYPE: PRT
<213> ORGANISM: Artificial Sequence
<220> FEATURE:
<223> OTHER INFORMATION: Synthetic Construct

<400> SEQUENCE: 119

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
                20                  25                  30

Leu Met Ala Asn Gly Ala Asp Val Asn Ala Lys Asp Glu Tyr Gly Leu
                35                  40                  45

Thr Pro Leu Tyr Leu Ala Thr Ala His Gly His Leu Glu Ile Val Glu
    50                  55                  60

Val Leu Leu Lys Asn Gly Ala Asp Val Asn Ala Val Asp Ala Ile Gly
65                  70                  75                  80

Phe Thr Pro Leu His Leu Ala Ala Phe Ile Gly His Leu Glu Ile Ala
                85                  90                  95

Glu Val Leu Leu Lys His Gly Ala Asp Val Asn Ala Gln Asp Lys Phe
                100                 105                 110

Gly Lys Thr Ala Phe Asp Ile Ser Ile Gly Asn Gly Asn Glu Asp Leu
                115                 120                 125

Ala Glu Ile Leu Gln Lys Leu Asn
    130                 135

<210> SEQ ID NO 120
<211> LENGTH: 136
<212> TYPE: PRT
<213> ORGANISM: Artificial Sequence
<220> FEATURE:
<223> OTHER INFORMATION: Synthetic Construct

<400> SEQUENCE: 120

Met Arg Gly Ser His His His His His His Gly Ser Asp Leu Gly Lys
1               5                   10                  15

Lys Leu Leu Glu Ala Ala Arg Ala Gly Gln Leu Asp Glu Val Arg Ile
                20                  25                  30

Leu Met Ala Asn Gly Ala Asp Val Asn Ala Lys Asp Glu Tyr Gly Leu
                35                  40                  45

Thr Pro Leu Tyr Leu Ala Thr Ala His Gly His Leu Glu Ile Val Glu
    50                  55                  60
```

Val Leu Leu Lys Asn Gly Ala Asp Val Asn Ala Val Asp Ala Ile Gly
65                  70                  75                  80

Phe Thr Pro Leu His Leu Ala Ala Phe Ile Gly His Leu Glu Ile Ala
                85                  90                  95

Glu Val Leu Leu Lys His Gly Ala Asp Val Asn Ala Gln Asp Lys Phe
            100                 105                 110

Gly Lys Thr Ala Phe Asp Ile Ser Ile Gly Asn Gly Asn Glu Asp Leu
        115                 120                 125

Ala Glu Ile Leu Gln Lys Leu Asn
    130                 135

<210> SEQ ID NO 121
<211> LENGTH: 136
<212> TYPE: PRT
<213> ORGANISM: Artificial Sequence
<220> FEATURE:
<223> OTHER INFORMATION: Synthetic Construct

<400> SEQUENCE: 121

Met Arg Gly Ser His His His His His His Gly Ser Asp Leu Gly Lys
1               5                   10                  15

Lys Leu Leu Glu Ala Ala Arg Ala Gly Gln Val Asp Glu Val Arg Ile
            20                  25                  30

Leu Met Ala Asn Gly Ala Asp Val Asn Ala Lys Asp Glu Tyr Gly Leu
        35                  40                  45

Thr Pro Leu Tyr Leu Ala Thr Ala His Gly His Leu Glu Ile Val Glu
    50                  55                  60

Val Leu Leu Lys Asn Gly Ala Asp Val Asn Val Asp Ala Ile Gly
65                  70                  75                  80

Phe Thr Pro Leu His Leu Ala Ala Phe Ile Gly His Leu Glu Ile Ala
                85                  90                  95

Glu Val Leu Leu Lys His Gly Ala Asp Val Asn Ala Gln Asp Lys Phe
            100                 105                 110

Gly Lys Thr Ala Phe Asp Ile Ser Ile Gly Asn Gly Asn Glu Asp Leu
        115                 120                 125

Ala Glu Ile Leu Gln Lys Leu Asn
    130                 135

<210> SEQ ID NO 122
<211> LENGTH: 103
<212> TYPE: PRT
<213> ORGANISM: Artificial Sequence
<220> FEATURE:
<223> OTHER INFORMATION: Synthetic Construct

<400> SEQUENCE: 122

Met Arg Gly Ser His His His His His His Gly Ser Asp Leu Gly Lys
1               5                   10                  15

Lys Leu Leu Glu Ala Ala Arg Ala Gly Gln Leu Asp Glu Val Arg Glu
            20                  25                  30

Leu Leu Lys Ala Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 123
<211> LENGTH: 103
<212> TYPE: PRT
<213> ORGANISM: Artificial Sequence
<220> FEATURE:
<223> OTHER INFORMATION: Synthetic Construct

<400> SEQUENCE: 123

Met Arg Gly Ser His His His His His Gly Ser Asp Leu Gly Lys
1               5                   10                  15

Lys Leu Leu Glu Ala Ala Arg Ala Gly Gln Leu Asp Glu Val Arg Glu
                20                  25                  30

Leu Ile Lys Ala Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 124
<211> LENGTH: 103
<212> TYPE: PRT
<213> ORGANISM: Artificial Sequence
<220> FEATURE:
<223> OTHER INFORMATION: Synthetic Construct

<400> SEQUENCE: 124

Met Arg Gly Ser His His His His His Gly Ser Asp Leu Gly Lys
1               5                   10                  15

Lys Leu Leu Glu Ala Ala Arg Ala Gly Gln Val Asp Glu Val Arg Glu
                20                  25                  30

Leu Leu Lys Ala Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 125
<211> LENGTH: 103
<212> TYPE: PRT
<213> ORGANISM: Artificial Sequence
<220> FEATURE:
<223> OTHER INFORMATION: Synthetic Construct

<400> SEQUENCE: 125

Met Arg Gly Ser His His His His His Gly Ser Asp Leu Gly Lys
1               5                   10                  15

-continued

```
Lys Leu Leu Glu Ala Ala Arg Ala Gly Gln Val Asp Glu Val Arg Glu
            20              25              30

Leu Ile Lys Ala Gly Ala Asp Val Asn Ala Lys Asp Lys Asp Gly Tyr
        35              40              45

Thr Pro Leu His Leu Ala Ala Arg Glu Gly His Leu Glu Ile Val Glu
        50              55              60

Val Leu Leu Lys Ala Gly Ala Asp Val Asn Ala Gln Asp Lys Phe Gly
65              70              75              80

Lys Thr Ala Phe Asp Ile Ser Ile Asp Asn Gly Asn Glu Asp Leu Ala
                85              90              95

Glu Ile Leu Gln Lys Leu Asn
            100
```